(12) United States Patent
Iwanari et al.

(10) Patent No.: US 7,875,705 B2
(45) Date of Patent: Jan. 25, 2011

(54) TUMOR DIAGNOSTIC AGENT USED IN PET COMPRISING ANTI-ROBO1 ANTIBODY

(75) Inventors: Hiroko Iwanari, Tochigi (JP); Isao Kohno, Chiba (JP); Takao Hamakubo, Tokyo (JP); Yoshitaka Kumakura, Tokyo (JP); Hirotaka Itoh, Tokyo (JP); Toshiko Sakihama, Tokyo (JP); Hiroyuki Aburatani, Tokyo (JP); Toshimitsu Momose, Tokyo (JP)

(73) Assignees: The University of Tokyo, Tokyo (JP); Perseus Proteomics Inc., Tokyo (JP)

( * ) Notice: Subject to any disclaimer, the term of this patent is extended or adjusted under 35 U.S.C. 154(b) by 485 days.

(21) Appl. No.: 11/946,220

(22) Filed: Nov. 28, 2007

(65) Prior Publication Data
US 2009/0092544 A1    Apr. 9, 2009

(30) Foreign Application Priority Data
May 28, 2007    (JP) .............................. 2007-140356

(51) Int. Cl.
    *C07K 16/00*    (2006.01)
(52) U.S. Cl. ................................. 530/387.1; 424/130.1
(58) Field of Classification Search ........................ None
    See application file for complete search history.

(56) References Cited

U.S. PATENT DOCUMENTS

| 5,994,524 | A | 11/1999 | Matsushima et al. |
| 6,713,278 | B1 | 3/2004 | Bouvier et al. |
| 7,329,509 | B2 | 2/2008 | Hamakubo et al. |
| 2005/0222391 | A1 | 10/2005 | Kodama et al. |
| 2007/0212359 | A1 | 9/2007 | Aburatani et al. |

FOREIGN PATENT DOCUMENTS

| EP | 0239400 A2 | 9/1987 |
| JP | 2001-333773 A | 12/2001 |
| JP | 2003-052370 A | 2/2003 |
| WO | 92/01047 A1 | 1/1992 |
| WO | 92/03918 A1 | 3/1992 |
| WO | 92/20791 A1 | 11/1992 |
| WO | 93/06213 A1 | 4/1993 |
| WO | 93/11236 A1 | 6/1993 |
| WO | 93/12227 A1 | 6/1993 |
| WO | 93/19172 A1 | 9/1993 |
| WO | 94/02602 A1 | 2/1994 |
| WO | 94/25585 A1 | 11/1994 |
| WO | 95/01438 A1 | 1/1995 |
| WO | 95/15388 A1 | 6/1995 |
| WO | 96/02576 A1 | 2/1996 |
| WO | 96/33735 A1 | 10/1996 |
| WO | 96/34096 A1 | 10/1996 |
| WO | 98/46777 A1 | 10/1998 |
| WO | 98/48051 A2 | 10/1998 |
| WO | 99/20764 A1 | 4/1999 |
| WO | 01/00828 A2 | 1/2001 |
| WO | 01/46697 A2 | 6/2001 |
| WO | 01/57207 A2 | 8/2001 |
| WO | 02/04514 A2 | 1/2002 |
| WO | 02/14500 A2 | 2/2002 |
| WO | 02/29103 A2 | 4/2002 |
| WO | 03/029488 A2 | 4/2003 |
| WO | 03/104453 A1 | 12/2003 |
| WO | 2005/095981 A1 | 10/2005 |

OTHER PUBLICATIONS

Tripathi et al. (Indian J. Cancer, vol. 44(2), pp. 62-71, Apr. 2007). Abstract only.*
Clin Cancer Res., vol. 12(11). pp. 3257-3264, Jun. 1, 2006.*
Ito et al., "Identification of ROBO1 as a Novel Hepatocellular Carcinoma Antigen and a Potential Therapeutic and Diagnostic Target," *Clin. Cancer Res.* 12(11): 3257-3264 (2006).
English Language Abstract of JP 2001-333773 A.
English Language Abstract of JP 2003-052370 A.
Loisel et al., "Recovery of homogeneous and functional $\beta_2$-adrenergic receptors from extracellular baculovirus particles" *Nat. Biotechnol.* 15(12):1300-1304 (1997).
Groth et al., "Production of Monoclonal Antibodies: Strategy and Tactics," *J. Immunol. Methods*, 35:1-21 (1980).
Tanaka et al., "The Generation of Monoclonal Antibodies against Human Peroxisome Proliferator-activated Receptors (PPARs)," *J. Atheroscler. Thrombo.*, 9(5):233-242 (2002).
Prasad et al. "Slit Protein-mediated Inhibition of CXCR4-induced Chemotactic and Chemoinvasive Signaling Pathways in Breast Cancer Cells," *J. Biol. Chem.* 279(10):9115-24 (2004).
Wang et al., "Induction of tumor angiogenesis by Slit-Robo signaling and inhibition of cancer growth by blocking Robo activity," *Cancer Cell* 4(1):19-29 (2003).

* cited by examiner

*Primary Examiner*—Misook Yu
*Assistant Examiner*—Meera Natarajan
(74) *Attorney, Agent, or Firm*—Greenblum & Bernstein, P.L.C.

(57) ABSTRACT

It is an object of the present invention to provide a novel antibody capable of specifically recognizing ROBO1 that is expressed in a cell membrane, a hybridoma that produces the above antibody, a method for producing the above antibody, and a tumor diagnostic agent used in PET comprising the above antibody. The present invention provides a monoclonal antibody capable of specifically recognizing ROBO1 existing on the surface of a cell, which is obtained by immunizing an animal to be immunized with a ROBO1-displaying budded baculovirus recovered from the culture supernatant of host cells infected with a recombinant baculovirus comprising the full-length cDNA of ROBO1 as an antigen.

5 Claims, 20 Drawing Sheets

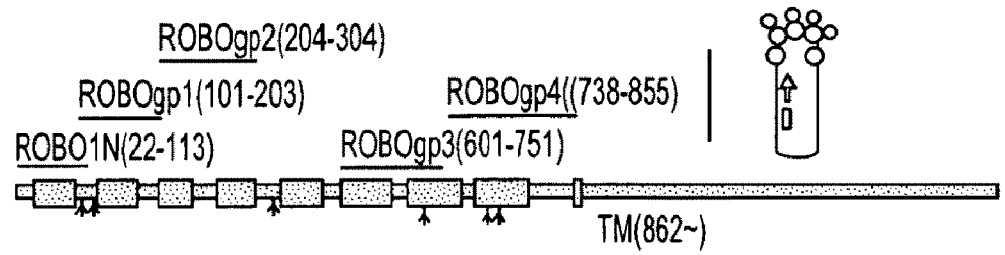
FIG. 1

```
ROBO1_ALX.ptn         1: MIAEPAHFYLFGLICLCSGSRLRQEDFPPRIVEHPSDLIVSKGEPATLNCKAEGRPTPTI      60
ROBO1_NM133631_AA     1: MIAEPAHFYLFGLICLCSGSRLRQEDFPPRIVEHPSDLIVSKGEPATLNCKAEGRPTPTI      60

ROBO1_ALX.ptn        61: EWYKGGERVETDKDDPPRSHRMLLPSGSLFFLRIVHGRKSRPDEGVYVCVARNYLGEAVSH    120
ROBO1_NM133631_AA    61: EWYKGGERVETDKDDPPRSHRMLLPSGSLFFLRIVHGRKSRPDEGVYVCVARNYLGEAVSH    120

ROBO1_ALX.ptn       121: NASLEVAILRDDFRQNPSDVMVAVGEPAVMECQPPRGHPEPTISWKKDGSPLDDKDERIT    180
ROBO1_NM133631_AA   121: NASLEVAILRDDFRQNPSDVMVAVGEPAVMECQPPRGHPEPTISWKKDGSPLDDKDERIT    180

ROBO1_ALX.ptn       181: IRGGKLMITYTRKSDAGKYVCVGTNMVGERESEVAELTVLERPSFVKRPSNLAVTVDDSA    240
ROBO1_NM133631_AA   181: IRGGKLMITYTRKSDAGKYVCVGTNMVGERESEVAELTVLERPSFVKRPSNLAVTVDDSA    240

ROBO1_ALX.ptn       241: EFKCEARGDPVPTVRWRKDDGELPKSRYEIRDDHTLKIRKVTAGDMGSYTCVAENMVGKA    300
ROBO1_NM133631_AA   241: EFKCEARGDPVPTVRWRKDDGELPKSRYEIRDDHTLKIPKVTAGDMGSYTCVAEMMVGKA    300

ROBO1_ALX.ptn       301: EASATLTVQ[VGSEPPHFVVEPRDQVVALGRTVTFQCEATGNPQPAIFWRREGSQNLLFSY]  360
ROBO1_NM133631_AA   301: EASATLTVQ[---EPPHFVVEPRDQVVALGRTVTFQCEATGNPQPAIFWRREGAQNLLFSY]  357

ROBO1_ALX.ptn       361: QPPQSSSRFSVSQTGDLTITNVQRSDVGYYICQTLNVAGSIITKAYLEVTDVIADRPPPV    420
ROBO1_NM133631_AA   358: QPPQSSSRFSVSQTGDLTITNVQRSDVGYYICQTLNVAGSIITKAYLEVTDVIADRPPPV    417

ROBO1_ALX.ptn       421: IRQGPVNQTVAVDGTFVLSCVATGSPVPTILWRKDGVLVSTQDSRIKQLENGVLQIRYAK    480
ROBO1_NM133631_AA   418: IRQGPVNQTVAVDGTFVLSCVATGSPVPTILWRKDGVLVSTQDSPIKQLENGVLQIRYAK    477

ROBO1_ALX.ptn       481: LGDTGRYTCIASTPSGEATWSAYIEVQEFGVPVQPPRPTDPNLIPSAPSKPEVTDVSRNT    540
ROBO1_NM133631_AA   478: LGDTGRYTCIASTPSGEATWSAYIEVQEFGVPVQPPRPTDPNLIPSAPSKREVTDVSRNT    537

ROBO1_ALX.ptn       541: VTLSWQPNLNSGATPTSYIIEAFSHASGSSWQTVAENVKTETSAIKGLKPNAIYLFLVRA    600
ROBO1_NM133631_AA   538: VTLSWQPNLNSGATPTSYIIEAFSHASGSSWQTVAENVKTETSAIKGLEPNAIYLFLVRA    597

ROBO1_ALX.ptn       601: ANAYGISDPSQISDPVKTQDVLPTSQGVDHKQVQPELGNAVLHLHNPTVLSSSSIEVHWT    660
ROBO1_NM133631_AA   598: ANAYGISDPSQISDPVKTQDVLPTSQGVDHKQVQPELGNAVLHLHNPTVLSSSSIEVHWT    657

ROBO1_ALX.ptn       661: VDQQSQYIQGYKILYRPSGANHGESDWLVFEVRTPAKNSVVIPDLREGVNYEIKARPFFN    720
ROBO1_NM133631_AA   658: VDQQSQYIQGYKILYRPSGANHGESDWLVFEVRTPAKNSVVIPDLREGVNYEIKARPFFN    717

ROBO1_ALX.ptn       721: EFQGADSEIKFAKTLEEAPSAPPQGVTVSFNDGNGTAILVSWQPPEDTQNGHVQEYKVW     780
ROBO1_NM133631_AA   718: EFQGADSEIEFAKTLEEAPSAPPQGVTVSFNDGNGTAILVSWQPPEDTQNGHVQEYKVW     777
```

FIG. 2

| | | |
|---|---|---|
| ROBO1_ALX.ptn | 781: CLGNETRYHINKTVDGSTFSVVIPFLVPGIPYSVEVAASTGAGSGVKSEPQFIQLDAHGN | 640 |
| ROBO1_NM133631_AA | 778: CLGNETRYHINKTVDGSTFSVVIPFLVPGIPYSVEVAASTGAGSGVKSEPQFIQLDAHGN | 837 |
| ROBO1_ALX.ptn | 841: PVSPEDQVSLAQQISDVVKQPAFIAGIGAACWIILMVFSIWLYPHRKKPNGLTSTYAGIP | 900 |
| ROBO1_NM133631_AA | 838: PVSPEDQVSLAQQISDVVKQPAFIAGIGAACWIILMVFSIWLYPHRKKPNGLTSTYAGIP | 897 |
| ROBO1_ALX.ptn | 901: KVPSFTFTPTVTYQRGGEAVSSGGPPGLLNISEPAAQPWLADTWPNTGNNHNDCSISCCT | 960 |
| ROBO1_NM133631_AA | 898: KVPSFTFTPTVTYQRGGEAVSSGGPPGLLNISEPAAQPWLADTWPNTGNNHNDCSISCCT | 957 |
| ROBO1_ALX.ptn | 1081: VEQNKLNKDYPANDTVPPTIPYNQSYDQNTGGSYNSSDPGSSTSGSQGHKKGARTPKVPK | 1140 |
| ROBO1_NM133631_AA | 1078: VEQNKLNKDYPANDTVPPTIPYNQSYDQNTGGSYNSSDPGSSTSGSQGHKKGAPTPKVPK | 1137 |
| ROBO1_ALX.ptn | 1141: QGGMNWADLLPPPPAHPPPHSNSEEYNISVDESYDQEMPCPVPPAPMYLQQDELEEEDE | 1200 |
| ROBO1_NM133631_AA | 1138: QGGMNWADLLPPPPAHPPPHSNSEEYNISVDESYDQEMPCPVPPAPMYLQQDELEEEDE | 1197 |
| ROBO1_ALX.ptn | 1201: RGPTPPVRGAASSPAAVSYSHQSTATLTPSPQEELQPMLQDCPEETGHMQHQPDPPPQPV | 1260 |
| ROBO1_NM133631_AA | 1198: RGPTPPVRGAASSPAAVSYSHQSTATLTPSPQEELQPMLQDCPEETGHMQHQPDPPPQPV | 1257 |
| ROBO1_ALX.ptn | 1261: SPPPPPPISPPHTYGYISGPLVSDMDTDAPEEEEDEADMEVAKMQTPPLLLPGLEQTPA | 1320 |
| ROBO1_NM133631_AA | 1258: SPPPPPPISPPHTYGYISGPLVSDMDTDAPEEEEDEADMEVAKMQTPPLLLPGLEQTPA | 1317 |
| ROBO1_ALX.ptn | 1321: SSVGDLESSVTGSMINGWGSASEEDNISSGPSSVSSSDGSFFTDADFAQAVAAAAEYAGL | 1380 |
| ROBO1_NM133631_AA | 1318: SSVGDLESSVTGSMINGWGSASEEDNISSGPSSVSSSDGSFFTDADFAQAVAAAAEYAGL | 1377 |
| ROBO1_ALX.ptn | 1381: KVARRQMQDAAGPPHFHASQCPRPTSPVSTDSNMSAAVMQKTPPAKKLKHQPGHLPPETY | 1440 |
| ROBO1_NM133631_AA | 1378: KVARRQMQDAAGPPHFHASQCPPPTSPVSTDSNMSAAVMQKTPPAEKLKHQPGHLPPETY | 1437 |
| ROBO1_ALX.ptn | 1441: TDDLPPPPVPPPAIKSPTAQSKTQLEVPPVVVPKLPSMDAPTDPSSDFKGSSYEGREVLD | 1500 |
| ROBO1_NM133631_AA | 1438: TDDLPPPPVPPPAIKSPTAQSKTQLEVPPVVVPKLPSMDAPTDPSSDRKGSSYEGREVLD | 1497 |
| ROBO1_ALX.ptn | 1501: GRQVVDMRTNPGDPPEAQEQQNDGKGPGNKAAKPDLPPAKTHLIQEDILPYCPPTFPTSN | 1560 |
| ROBO1_NM133631_AA | 1498: GRQVVDMRTNPGDPPEAQEQQNDGKGPGNKAAKPDLPPAKTHLIQEDILPYCPPTFPTSN | 1557 |
| ROBO1_ALX.ptn | 1561: NPPDPSSSSSMSSRGSGSRQREQANVGRRNIAEMQVLGGYEPGEDMNEELEETES | 1615 |
| ROBO1_NM133631_AA | 1558: NPPDPSSSSSMSSRGSGSRQREQANVGRRNIAEMQVLGGYEPGEDMNEELEETES | 1612 |

*FIG. 2 (cont.)*

Fig. 3
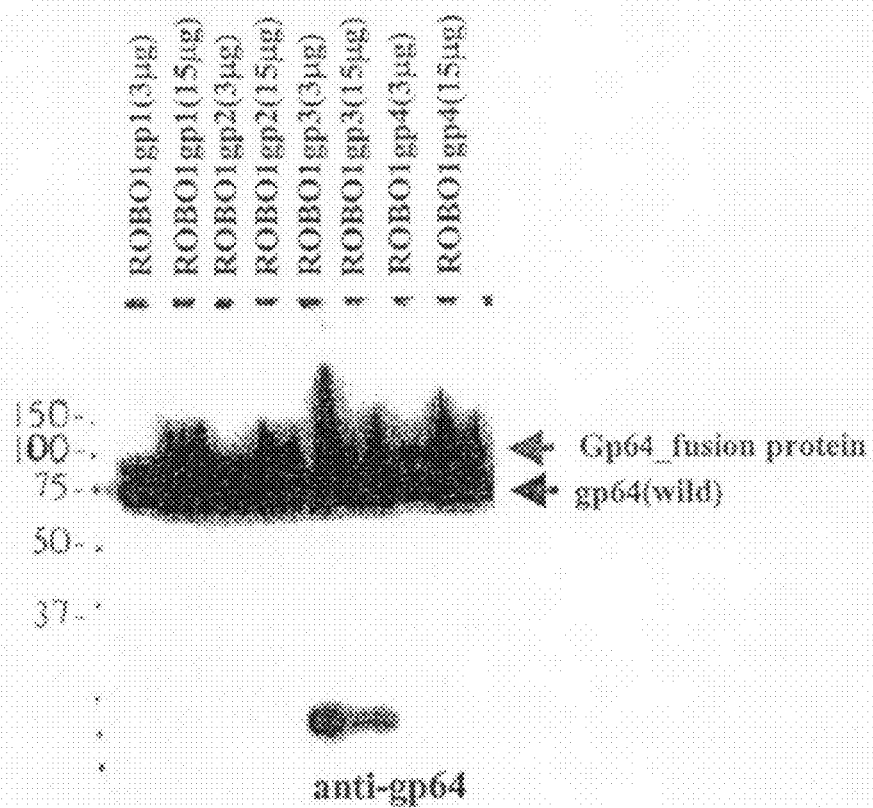
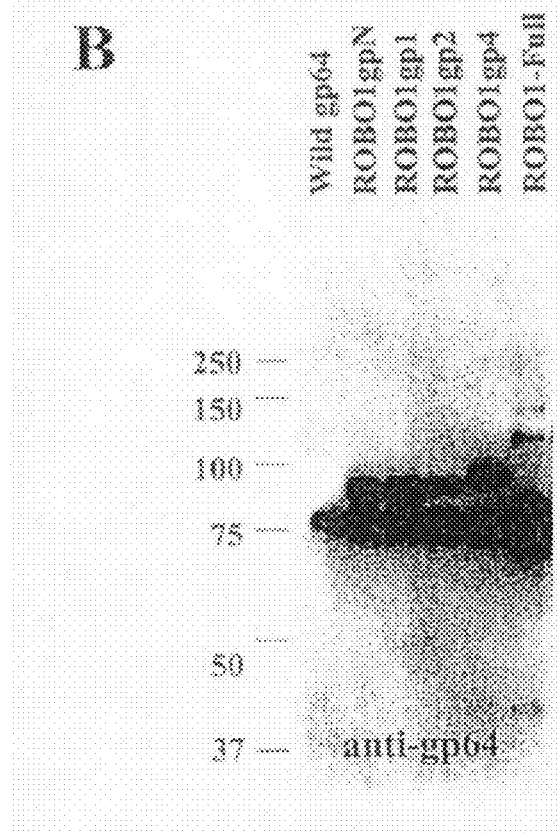
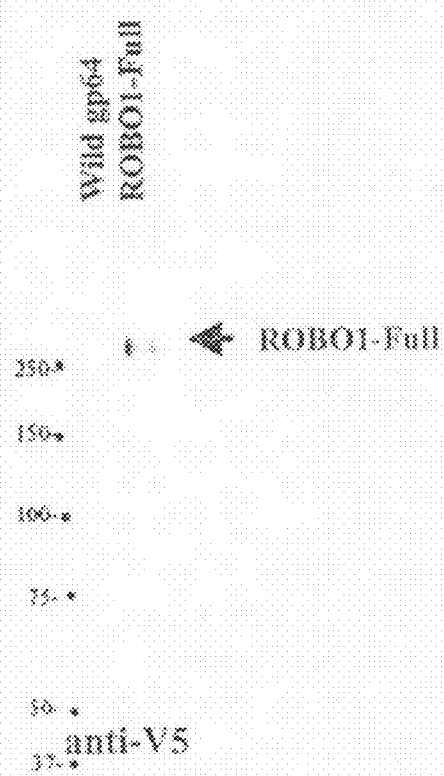

Fig. 7
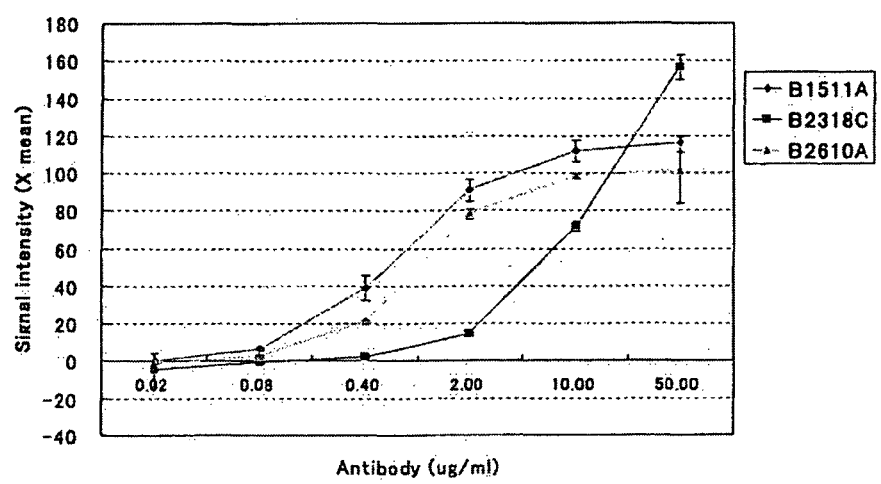
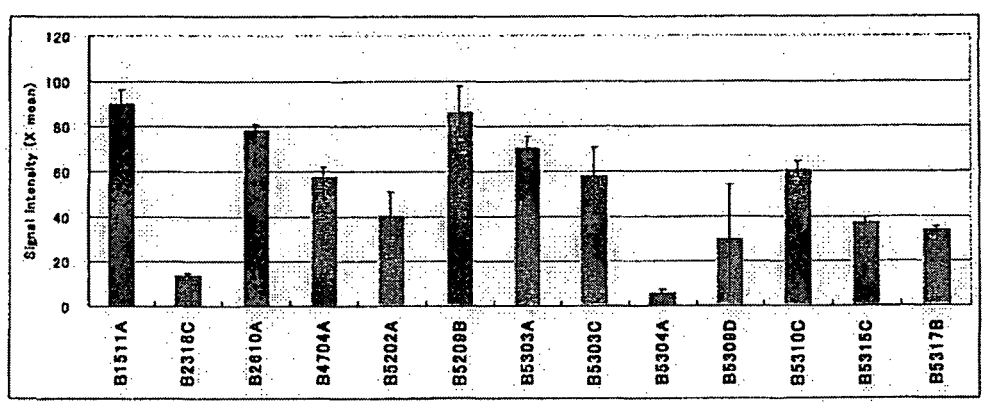
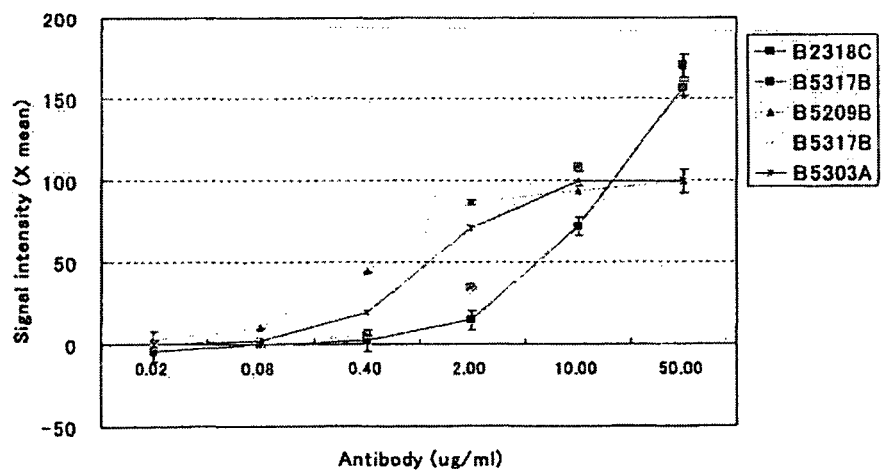

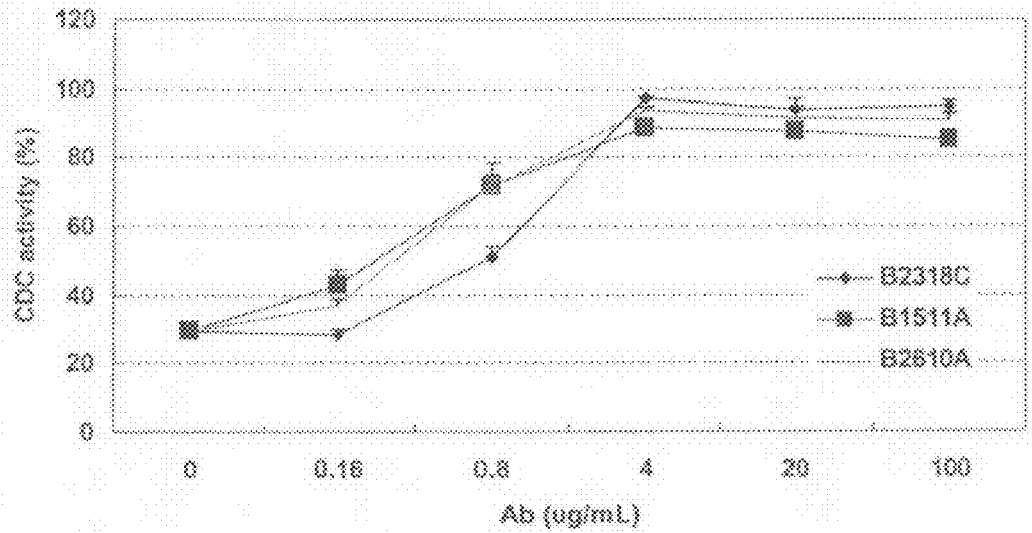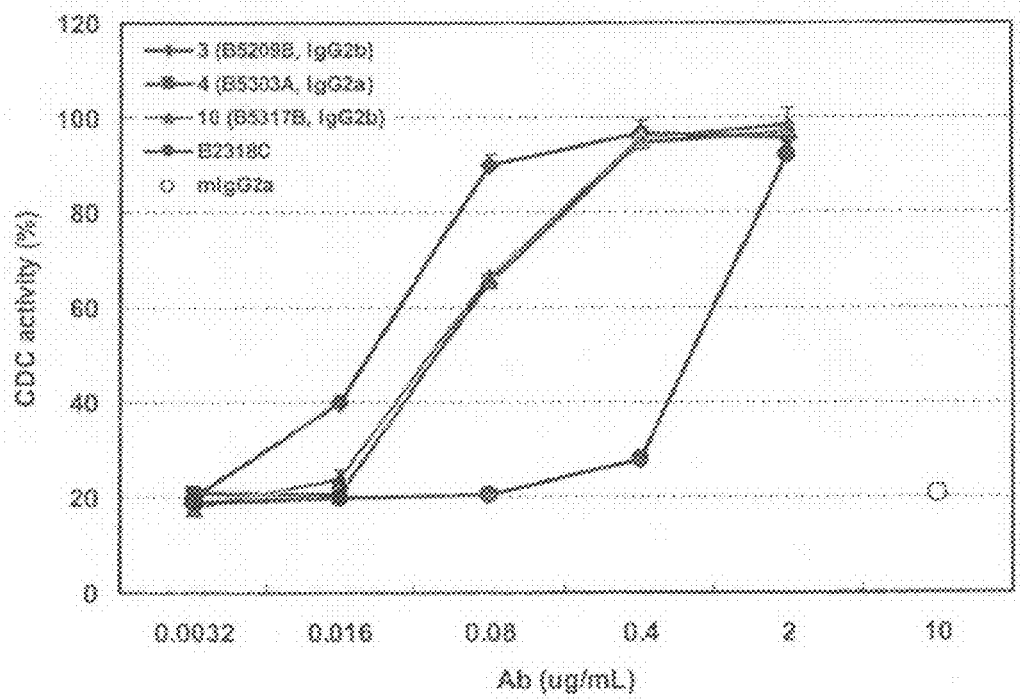
Fig. 8

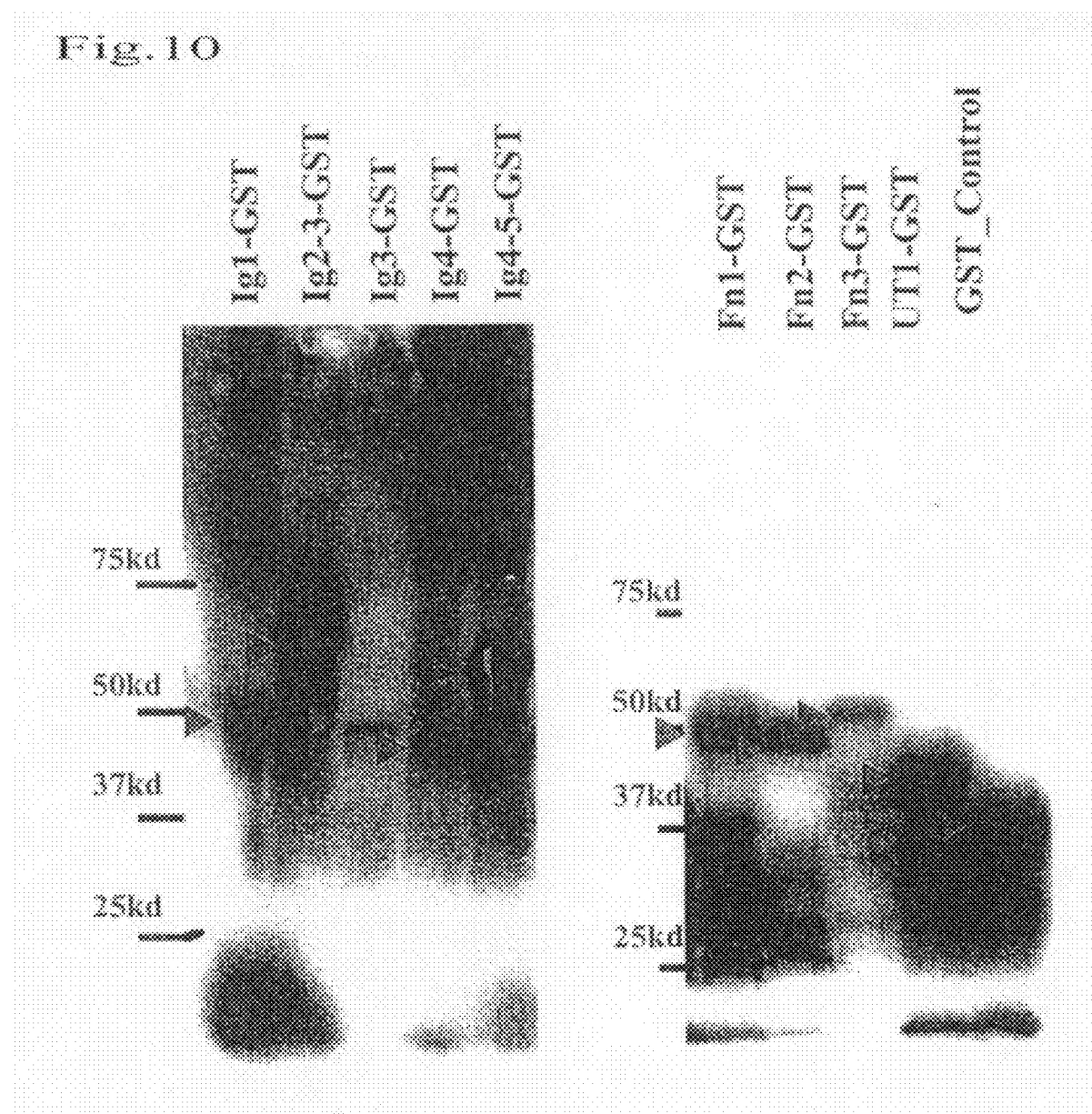

Fig. 12
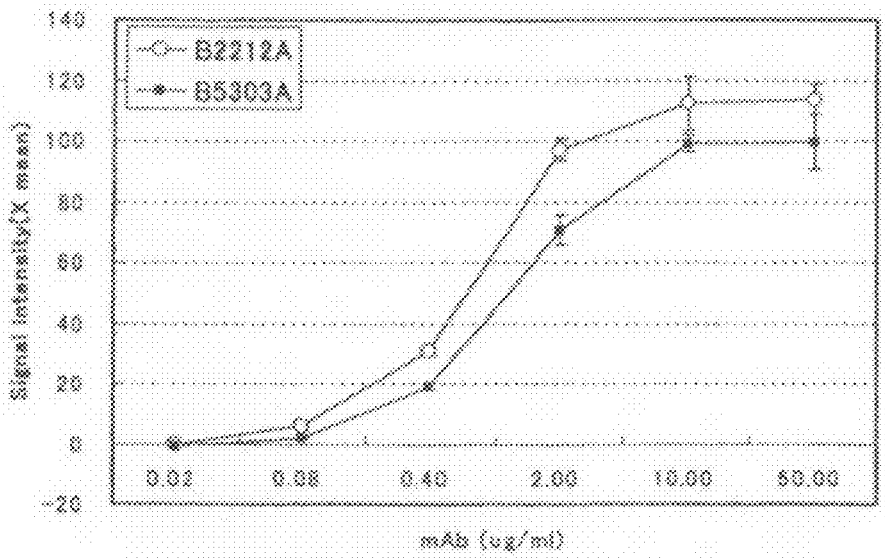
A
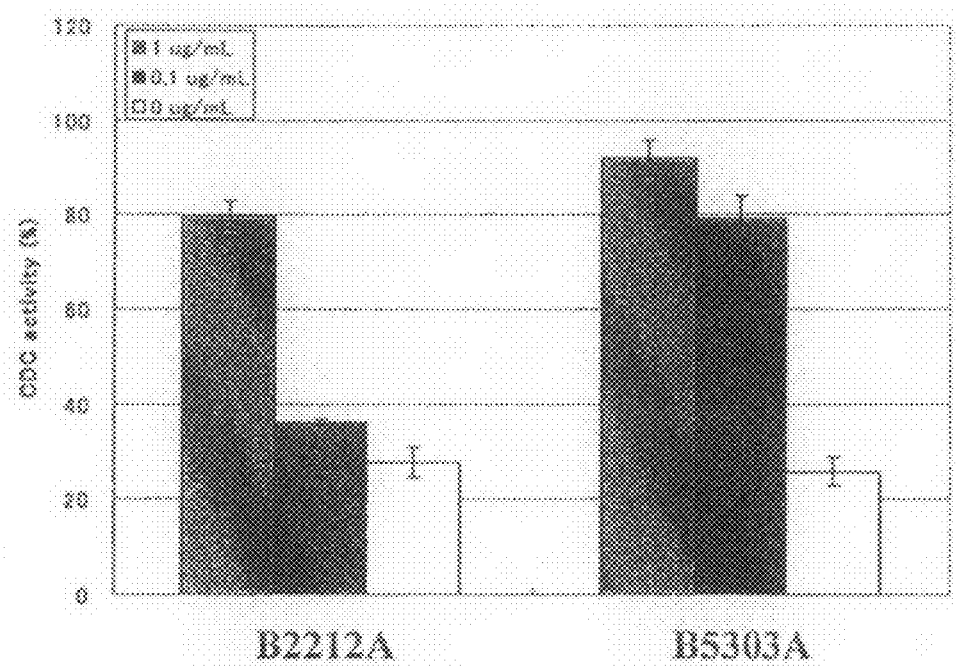
B

TUMOR DIAGNOSTIC AGENT USED IN PET COMPRISING ANTI-ROBO1 ANTIBODY

TECHNICAL FIELD

The present invention relates to an antibody that recognizes ROBO1, a hybridoma that produces the above antibody, a method for producing the above antibody, and a tumor diagnostic agent used in PET, which comprises the above antibody.

BACKGROUND ART

Primary hepatocellular carcinoma is carcinoma with poor prognosis, which ranked third (13%) in men and fourth (9.0%) in women with regard to death by carcinoma, a primary cause of death in Japan in 2001 (excerpt from "Population Survey Report" Statistics and Information Department, Minister's Secretariat, the Ministry of Health, Labour, and Welfare). The number of chronic patients has increased due to virus infection year after year, and a majority of such patients develop hepatocirrhosis and then hepatocellular carcinoma in many cases. Under such circumstances, it has been extremely strongly desired that an early diagnostic method applied at stages ranging from such hepatocirrhosis to hepatocellular carcinoma and a method for treating hepatocellular carcinoma be developed. If a breakthrough resolution were not found, the number of people dying would increase over the next 10 to 15 years. As a diagnostic method, such hepatocellular carcinoma is comprehensively evaluated on the basis of biochemical data such as the values of GOP/GTP, alkaline phosphatase, albumin, etc. in serum or the value of AFP (α-photoprotein) used as a tumor marker, and diagnostic imaging. Thereafter, if necessary, a small amount of piece of tissue is collected by a needle biopsy, and a confirmed diagnosis is carried out based on pathological determination. At present, a tumor marker has been used particularly in the diagnosis of hepatocellular carcinoma The positive rate of α-photoprotein (AFP), the most commonly used tumor marker, in patients with hepatocellular carcinoma is approximately 60 to 70%. However, such a positive result may also be obtained, when a subject is a patient with a chronic liver disease or a pregnant woman. In addition, the positive rate of PIVKA-II, a tumor marker for hepatic carcinoma, is low (somewhat lower than 50%), but the specificity of this marker to hepatocellular carcinoma is considered higher than that of AFP. Currently, such two types of examinations have mainly been conducted. At any rate, since false positive or double negative cases exist, it is anticipated that a tumor marker having high specificity be developed.

In recent years, a gene analysis technique using a high-performance array such as a DNA microarray has been developed, and thus all-inclusive and comprehensive analyses of gene expression in carcinoma have become practicable. A change in the expression level of mRNA in cancer tissues is analyzed by a DNA microarray analysis method, and a gene group associated with malignant degeneration of carcinoma due to multistep factors, invasion or metastasis of cancer cells, etc. has been comprehensively identified. Moreover, it is expected that several numbers of new findings regarding the new properties of cancer cells will be obtained by clarifying the individual physiological functions of such an identified gene group. Thus, identification of molecules, the expression of which is accentuated or decreased in various types of carcinomas, has been progressing.

ROBO1, a hepatocellular carcinoma-specific expression molecule, is a type I membrane protein that is a member of the immunoglobulin superfamily, to which N-CAM, DCC, L1-CAM, etc. belong. ROBO1 has 5 immunoglobulin domains and 3 fibronectin III domains in the extracellular region thereof. The amino acid sequence is highly conserved in various organisms ranging from a fly to a human. It shows amino acid sequence homology of 34% with C. elegans, 33% with Dorosofila, 96% with a mouse, and 95% with a rat. A fly homolog of ROBO1 has been cloned as a molecule that controls the median crossing of an axial filament in gene screening studies of fruit flies. It has been reported that such a fly homolog is a Slit protein receptor. In addition, by another study group, ROBO1 has also been identified as Dutt1 (Deleted U Twenty Twenty), a molecule existing in a homozygous missing region in the chromosomal region 3p12 of U2020 that is a cell line of lung small cell carcinoma With regard to ROBO1, loss of heterozygosity (LOH) at chromosome is detected at a high frequency in lung cancer, breast cancer, and kidney cancer. Due to methylation of a promoter region in the other allele, the expression thereof is suppressed. Such facts suggest the possibility of ROBO1 as a cancer suppressor gene. In the case of ROBO1 homozygous deficient mice, it has been reported that half of the mice die during the prenatal period, and that the surviving half mice also lead to death due to pulmonary hypoplasia. In addition, in the case of ROBO1 heterozygous deficient mice, the incidence of cancer 1 year or more after the birth is 3 times higher than that of normal mice. From this fact as well, ROBO1 is considered to be a cancer suppressor gene. Moreover, the expression of a Slit2 gene that is a ROBO1 ligand is also suppressed by methylation or the like in many types of carcinomas. In a test using a conditioning medium of Slit2 or the like, Slit2 exhibited proliferative inhibitory action and apoptotic action towards a lung cancer cell line, a breast cancer cell line, and a colon cancer cell line. Thus, Slit2 is also considered to be a candidate molecule for a cancer suppressor gene. As a completely different finding, Wang et al. has reported that ROBO1 is expressed in neovascularity, and that the expression of Slit2 is accentuated in cancer cells and it is associated with vascularization in cancer cells.

Furthermore, identification of ROBO1 as a hepatocellular carcinoma antigen, the potential treatment of hepatocellular carcinoma using an anti-ROBO1 monoclonal antibody towards a ROBO1 antigen as a target, and the potential serodiagnosis of hepatocellular carcinoma using a soluble-type ROBO1 as an indicator, have also been reported (Non-patent document 1).

On the other hand, the diagnostic imaging of tumor is carried out using CT or MRI. However, in some cases, it is difficult for CT or MRI to carry out differentiation of benign tumor from malignant tumor, diagnosis of recurrence after surgery, differentiation of the tumor from other pathologic lesions, even using a contrast medium. Recently, Positrom Emission Tomography (PET) using $^{18}$F-2-fluoro-2-deoxy-glucose ($^{18}$F-FDG) has been used as a diagnostic imaging to assist CT or MRI. However, since $^{18}$F-FDG is accumulated even in normal tissues (for example, brain, etc.) involving active glucose metabolism or in inflammatory tissue at an acute stage, as a diagnostic mechanism using $^{18}$F-FDG, it has been difficult to make a diagnosis in some types of a tumor. Moreover, in drug discovery, molecular imaging is a technique of visualizing a small amount of molecule existing in a living body, such as a protein molecule in a living body, using such amount as an indicator, and further quantifying the dynamics. In particular, such a method using PET is excellent in terms of detection sensitivity and quantitative capability. In particular, PET used for small animals is expected to drastically accelerate in-vivo translational research and to have an impact on innovative changes in a drug discovery process.

Non-patent document 1: Ito H, et al, Identification of ROBO1 as a nobel hepatocellular carcinoma antigen and a potential therapeutic and diagnostic target. Clin Cancer Res. 2006 Jun. 1; 12(11 Pt 1):3257-64.

DISCLOSURE OF THE INVENTION

An Object to be Solved by the Invention

It is an object of the present invention to provide a novel antibody capable of specifically recognizing ROBO1 that is expressed in a cell membrane, a hybridoma that produces the above antibody, a method for producing the above antibody, and a tumor diagnostic agent used in PET comprising the above antibody. It is a particular object of the present invention to provide a tumor diagnostic agent used in PET that is capable of diagnosing hepatic carcinoma.

A Means for Solving the Object

In general, it is not easy to produce a monoclonal antibody that specifically detects a membrane protein molecule with high sensitivity. One reason is that it is not easy to prepare an antigen. Further, the function of such a membrane protein is biologically particularly important in many cases, and high homology is conserved across species. Thus, it is anticipated that a mouse is in a state of immunologic tolerance to an antigen site. In the present invention, a virus display antigen that had applied a baculovirus expression system was used as an immunogen. Thereafter, a transgenic mouse, in which gp64 used as a major protein of the viral antigen had been allowed to excessively express, was immunized with the immunogen. Thus, an attempt was made to suppress generation of an antibody reacting with the virus and to specifically produce a monoclonal antibody reacting with ROBO1. As a result, the present inventors have succeeded in obtaining a monoclonal antibody capable of specifically recognizing ROBO1 existing on the surface of a cell. Moreover, the inventors have found that an excellent tumor diagnostic agent used in PET can be provided by labeling the aforementioned monoclonal antibody with a radioactive metal. The present invention has been completed based on such findings.

That is to say, the present invention provides the following features.

(1) A monoclonal antibody capable of specifically recognizing ROBO1 existing on the surface of a cell, which is obtained by immunizing an animal to be immunized with a ROBO1-displaying budded baculovirus recovered from the culture supernatant of host cells infected with a recombinant baculovirus comprising the fill-length cDNA of ROBO1 as an antigen.

(2) The monoclonal antibody according to (1) above, wherein the animal to be immunized is a transgenic mouse in which gp64 is excessively expressed.

(3) The monoclonal antibody according to (1) above, which is selected by screening using a cell, on the surface of which ROBO1 is expressed.

(4) The monoclonal antibody according to (1) above, which is produced from a hybridoma having accession No. FERM BP-10921.

(5) A hybridoma, which produces the monoclonal antibody according to (1).

(6) A hybridoma having accession No. FERM BP-10921.

(7) A method for producing the monoclonal antibody according to (1) above, which comprises: immunizing an animal to be immunized with a ROBO1-displaying budded baculovirus recovered from the culture supernatant of host cells infected with a recombinant baculovirus comprising the full-length cDNA of ROBO1 as an antigen; recovering antibody-generating cells from the immunized animal; culturing a hybridoma produced using the antibody-generating cells; and allowing the hybridoma to produce a monoclonal antibody capable of specifically recognizing ROBO1 existing on the surface of a cell.

(8) A tumor diagnostic agent used in PET, which comprises the monoclonal antibody according to (1) above labeled with a radioactive metal.

(9) The tumor diagnostic agent used in PET according to (8) above, wherein the radioactive metal is $^{64}$Cu.

Effect of the Invention

The present invention provides a novel antibody capable of specifically recognizing ROBO1, which is allowed to express in a cell membrane. The present invention further provides a tumor diagnostic agent used in PET, which comprises the above antibody. By extracorporeally imaging a tumor using the tumor diagnostic agent used in PET of the present invention so as to examine expansion (invasion or metastasis) of a pathologic lesion, it becomes possible to enhance precision of a diagnosis. Moreover, by the combined use of the above tumor diagnostic agent with an internal treatment with a radioactive ray, external application of a radioactive ray, ultrasonic therapy, thermal therapy, etc., it becomes possible to extend the possibility of such a treatment and to improve a cure rate.

BEST MODE FOR CARRYING OUT THE INVENTION

The present invention will be described in detail below.

(1) ROBO1 used as antigen

In order to analyze expression of ROBO1 at a protein level, an anti-ROBO1 antibody having high specificity is required. In the present invention, an anti-ROBO1 monoclonal antibody was produced. ROBO1 shows homology of 95% or more at the amino acid sequence level with a mouse. Thus, in the present invention, a common immunization method was not used, but two types of methods, namely, a method of immunizing a gp64-expressing transgenic mouse with a budded baculovirus antigen (BV antigen) and a method of immunizing a MRL/lpr mouse with a soluble-type ROBO1 purified antigen (sROBO1-His) were adopted. ROBO1 has domains characteristic for an extracellular region, namely, 5 immunoglobulin domains and 3 fibronectin III domains. Thus, while maintaining each of the aforementioned domains, a Gp64-bound antigen was designed.

That is to say, the monoclonal antibody of the present invention that is capable of specifically recognizing ROBO1 existing on the surface of a cell is characterized in that it is obtained by immunizing an animal to be immunized with a ROBO1-displaying budded baculovirus recovered from the culture supernatant of host cells infected with a recombinant baculovirus comprising the full-length cDNA of ROBO1 as an antigen. The animal to be immunized is preferably a transgenic mouse, which excessively expresses gp64.

The full-length cDNA of ROBO1 may be either the cDNA of a wild-type ROBO1, or the cDNA of mutant ROBO1. A mutant desirably has an amino acid sequence, which shows identity of at least 80%, preferably 90% or more, and more preferably 95% or more, with the amino acid sequence of wild-type ROBO1. Amino acid residues to be mutated are preferably mutated with other amino acid residues in which the properties of an amino acid side chain are conserved. Examples of the properties of such an amino acid side chain include hydrophobic amino acids (A, I, L, M, F, P, W, Y, and V), hydrophilic amino acids (R, D, N, C, E, Q, G, H, K, S, and T), amino acids having an aliphatic side chain (G, A, V, L, I, and P), amino acids having a hydroxyl group-containing side chain (S, T, and Y), amino acids having a sulfur atom-containing side chain (C and M), amino acids having a carboxylic acid- and amide-containing side chain (D, N, E, and Q), amino acids having a base-containing side chain (R, K, and H), and amino acids having an aromatic series-containing side chain (H, F, Y, and W) (wherein the characters in parentheses indicate amino acids, each of which is indicated with a single character). Persons skilled in the art are able to introduce mutation into amino acids of a certain protein according to a known method such as site-directed mutagenesis, as appropriate, so as to prepare a protein equivalent to the certain protein.

In the present invention, a ROBO1-displaying budded baculovirus recovered from the culture supernatant of host cells infected with a recombinant baculovirus comprising the full-length cDNA of ROBO1 is used as an antigen. A method of preparing such a ROBO1-displaying budded baculovirus used as an antigen is known. Thus, such a ROBO1-displaying budded baculovirus can be prepared according to the methods described in JP Patent Publication (Kokai) No. 2001-333773 A; JP Patent Publication (Kokai) No. 2003-52370 A; Loisel T P, Ansanay H, St-Onge S, Gay B, Boulanger P. Strosberg A D, Marullo S, Bouvier M., Nat. Biotechnol. 1997 November; 15(12): 1300-4, Recovery of homogeneous and functional beta 2-adrenergic receptors from extracellular baculovirus particles; and International Publication WO98/46777, for example.

Specifically, at least one type of recombinant baculovirus comprising the full-length cDNA of ROBO1 is used. Baculovirus, which transmits to insects and develops disease therein, is an envelope virus having cyclic double-stranded DNA as a gene. This virus shows sensitivity to insects belonging to *Lepidoptera, Hymenoptera, Diptera*, etc. Examples of baculovirus used in the present invention include *Autographa californica* NPV (AcNPV) of a gamma moth subfamily of NPV and *Bombyx mori* NPV (BmNPV) of a silk worm. Such a virus can be used as a vector. An example of host cells (infected and subcultured cells) of AcNPV is *Spodoptera frugiperda* cells (Sf cells). An example of host cells (infected and subcultured cells) of BmNPV is BmN4 cells. Such Sf cells have a growth rate higher than that of such BmN4 cells. In addition, AcNPV has ability to transmit to human liver cells and human embryonic kidney cells. Thus, an AcNPV vector is preferable. As a host, *Spodoptera Frugiperda* cell lines Sf9 and Sf21 have been established from the ovarian tissues of *S. frugiperda* larva Such cell lines are available from several manufacturers such as Invitrogen or Pharmingen (San Diego, Calif.), or are also available from ATCC. Otherwise, it is also possible to use a living insect larva as a host cell line.

A recombinant virus used in the present invention may be constructed according to a common method. A recombinant virus can be constructed by the following procedures, for example. First, a protein gene to be expressed is inserted into a transfer vector, so as to construct a recombinant transfer vector. The total size of a transfer vector is generally between approximately several kb to 10 kb. Approximately 3 kb out of the size is a skeleton derived from a plasmid, and it comprises an antibiotic resistance gene that is resistance to antibiotics such as ampicillin and an initiation signal in bacteria DNA replication. A common transfer vector comprises the 5'- and 3'-regions of a polyhedron gene (several kb for each), as well as the aforementioned skeleton. A homologous recombination occurs in these sequences between a gene of interest and the polyhedron gene, when transfection as described below is carried out. Moreover, such a transfer vector preferably comprises a promoter for expression of a protein gene. Examples of such a promoter include a polyhedron gene promoter, a p10 gene promoter, and a capsid gene promoter. The type of such a transfer vector is not particularly limited. Specific examples of a transfer vector include: AcNPV transfer vectors such as pEVmXIV2, pAcSG1, pVL1392/1393, pAcMP2/3, pAcJP1, pAcUW21, pAcDZ1, pBlueBacIII, pAcUW51, pAcAB3, pAc360, pBlueBacHis, pVT-Bac33, pAcUW1, or pAcUW42/43; and BmNPV transfer vectors such as pBK283, pBK5, pBB30, pBE1, pBE2, pBK3, bPK52, pKBblue, pBKblue2, or pBF series (which are available from Funakoshi Corporation, Fujisawa Pharmaceutical Co., Ltd., etc.).

Subsequently, in order to produce a recombinant virus, the aforementioned recombinant transfer vector is mixed with a virus, and the mixture is then introduced into a cultured cell used as a host. Otherwise, the aforementioned transfer vector is introduced into a cultured cell used as a host, which has previously been infected with a virus. Thus, a homologous recombination is allowed to occur between the recombinant transfer vector and the virus genomic DNA, so as to construct a recombinant virus. Examples of the cultured cell used as a host herein include the aforementioned hosts. In general, the cultured insect cells (Sf9 cells, BmN cells, etc.) can be used. Culture conditions are selected by persons skilled in the art, as appropriate. Specifically, when Sf9 cells are used, it is preferable to carry out the culture around 28° C. in a medium that contains 10% fetal bovine serum. The thus constructed recombinant virus can be purified by a common method such as plaque assay. In the thus produced recombinant virus, foreign DNA is substituted with or inserted into the gene region of the polyhedron protein of a nuclear polyhedrosis virus, and thus a polyhedron cannot be formed. Accordingly, such a recombinant virus is easily distinguishable from a non-recombinant virus.

In the method of the present invention, the aforementioned suitable host (the cultured cells of *Spodoptera frugiperda* cell lines Sf9 and Sf21, insect larva, etc.) is infected with the aforementioned recombinant baculovirus. After a certain period of time (72 hours later, for example) has passed, an extracellular budded virus (budded virus, BV) can be recovered from the culture supernatant by a separation operation such as centrifugation. Such an extracellular budded baculovirus can be recovered as follows. First, the culture of the infected cells is centrifuged at 500 to 3,000 g, so as to recover a supernatant that contains an extracellular budded baculovirus. Thereafter, the supernatant is centrifuged at approximately 30,000 to 50,000 g, so as to obtain a precipitate that contains the extracellular budded baculovirus.

Exogenous expression of a protein is important for carrying out biological analysis. In the case of a membrane protein, however, because of the hydrophobic properties thereof, a suitable system capable of expressing a protein in an amount sufficient for the analysis has not yet been established. Under such circumstances, an expression system using baculovirus and insect cells is used as a system that is expected to enable high-quality expression for both water-soluble and membrane proteins. Such a baculovirus expression system is advantageous in that it enables posttranslational modification such as fatty acid acylation or phosphorylation, which does not generally occur in expression using *Escherichia coli*. In addition, when such a baculovirus expression system is compared with yeast, since the recovery of the expressed protein is not inhibited by a cell wall, differing from the case of yeast, the treatment of cells is comparatively easy. In the case of using animal cells, posttranslational modification necessary for functions is expected, but expression of a large amount of membrane protein is difficult. It has been reported that a high expression level is expected from the baculovirus expression system, but that premature proteins may increase at times, resulting in agglutination or decomposition.

The type of the antibody of the present invention is not particularly limited. Examples of an antibody used herein include a mouse antibody, a human antibody, a rat antibody, a rabbit antibody, a sheep antibody, a camel antibody, a chicken antibody, and a gene recombinant antibody that is artificially modified for the purpose of decreasing heterogenetic antigenecity to a human or other purposes, such as a chimeric antibody or a humanized antibody. Such a gene recombinant antibody can be produced by a known method. A chimeric antibody is an antibody consisting of the heavy-chain and light-chain variable region of a mammal antibody other than a human antibody, such as a mouse antibody, and the heavy-chain and light-chain constant region of a human antibody. DNA encoding the variable region of a mouse antibody is ligated to DNA encoding the constant region of a human antibody. The ligated product is then incorporated into an expression vector, and the vector is then introduced into a host, so as to obtain such a chimeric antibody. A humanized antibody is produced by transplanting the complementarity determining region (CDR) of a mammal antibody other than a human antibody, such as a mouse antibody, into the complementarity determining region of a human antibody. A common gene recombinant technique applied to produce such a humanized antibody is known. Specifically, a DNA sequence designed such that the CDR of a mouse antibody is ligated to the framework region (FR) of a human antibody is synthesized from several oligonucleotides produced such that they have an overlapped portion at the termiri thereof according to the PCR method. The obtained DNA is ligated to DNA encoding the constant region of a human antibody, and the thus ligated product is then incorporated into an expression vector. The thus obtained vector is introduced into a host, so that the host can produce a humanized antibody UP Patent No. 239400, International Publication WO96/02576, etc.).

Moreover, a method of obtaining a human antibody is also known. For example, a human lymphocyte is sensitized with a desired antigen or a cell that expresses such a desired antigen in vitro. The sensitized lymphocyte is then fused with a human myeloma cell such as U266, so as to obtain a desired human antibody having bindability to an antigen (JP Patent Publication Kokoku) No. 1-59878 B (1989)). In addition, antigenic animal having all repertories of human antibody genes is immunized with a desired antigen, so as to obtain a desired human antibody (refer to WO93/12227, WO92/03918, WO94/02602, WO94/25585, WO96/34096, and WO96/33735). Moreover, a technique of obtaining a human antibody by panning a human antibody library is known. For example, the variable region of a human antibody is allowed to express on a phage as a single-stranded antibody (scFv) according to the phage display method, and a phage binding to an antigen can be selected. By analyzing the gene of the selected phage, a DNA encoding the variable region of a human antibody binding to an antigen can be determined. If the DNA sequence of scFv binding to such an antigen is determined, the obtained sequence is incorporated into a suitable expression vector, and as a result, a human antibody can be obtained. Such methods have already been known, and are described in WO92/01047, WO92/20791, WO93/06213, WO93/11236, WO93/19172, WO95/01438, and WO95/15388.

Furthermore, the aforementioned antibodies may also be low molecular weight antibodies such as antibody fragments or modified antibodies, unless they lose the property of recognizing the entire length or a part of a protein encoded by a ROBO1 gene. Specific examples of an antibody fragment include Fab, Fab', F(ab')2, Fv, and Diabody. In order to obtain such an antibody fragment, a gene encoding such an antibody fragment may be constructed, it may be then introduced into an expression vector, and it may be then allowed to express in suitable host cells.

As a modified antibody, an antibody that binds to various types of molecules such as polyethylene glycol (PEG) can be used. Further, it is also possible to bind a radioisotope, a chemotherapeutic, or the like to an antibody. A radiolabeled antibody is particularly useful. Such a modified antibody can be obtained by chemical modification of the obtained antibody. It is to be noted that a method of modifying an antibody is known to persons skilled in the art.

A method of producing the monoclonal antibody of the present invention and a hybridoma is known in the present technical field (Campbell, "Monoclonal Antibody Technology: Laboratory Techniques in Biochemistry and Molecular Biology," Elsevier Science Publishers, Amsterdam, The Netherlands, 1984; St. Groth et al., J. Immunol. Methods 35: 1-21, 1980). A protein or a fragment thereof encoded by a DKK1 gene is used as an immunogen. Such an immunogen is subcutaneously or intraperitoneally injected into any given animal (a mouse, a rabbit, etc.) that is known to produce an antibody, so that the animal can be immunized. For such immunization, an adjuvant may also be used. Such an adjuvant is known to persons skilled in the art.

A monoclonal antibody can be obtained by excising splenic cells from the immunized animal, and fusing the splenic cells with myeloma cells, so as to produce hybridoma cells that produce a monoclonal antibody. Methods well known in the present technical field, such as ELISA assay, Western blot analysis, radioimmunoassay, or FACS using cells that express ROBO1 on the surfaces thereof, can be used to select hybridoma cells that produce an antibody recognizing ROBO1. A hybridoma that secretes a desired antibody is cloned, and the cloned cells are then cultured under suitable conditions. Thereafter, the secreted antibodies are recovered and are then purified by a method well known in the present technical field, such as use of an ion-exchange column or affinity chromatography.

DNA encoding such a monoclonal antibody can easily be isolated and sequenced by a commonly used method (for example, using an oligonucleotide probe capable of specifically binding to a gene encoding the heavy chain and light chain of a monoclonal antibody). A hybridoma cell is a preferred starting material of such DNA. Once such DNA is isolated, it is then inserted into an expression vector. Thereafter, the vector is introduced into host cells such as *E. coli* cells, COS cells, CHO cells, or myeloma cells that do not produce immunoglobulin unless they are transformed. Thereafter, a monoclonal antibody can be produced from the recombinant host cells.

Since expression of a ROBO1 gene is accelerated in specific cancer tissues, the antibody of the present invention is also useful as a cancer diagnostic marker. A certain method such as the Western blot method, the ELISA method, or histological staining is applied to the antibody of the present invention, so that expression of a protein encoded by the ROBO1 gene can be detected in tissues or cells. A sample derived from the tissues of a subject (for example, a biopsy sample, a blood sample, etc.) is allowed to come into contact with the antibody of the present invention under conditions wherein an immune complex can be formed, and whether or not the aforementioned antibody binds to the aforementioned sample is determined. As a result, the presence or amount of a protein encoded by the ROBO1 gene contained in the aforementioned sample can be determined. Thereby, the diagnosis of cancer, the monitoring of progression or cure of cancer, and prediction of prognosis can be carried out. Examples of a biological sample include (a) tissues, (b) the culture of the collected tissues, (c) a tissue extract, (d) the sputum of a cancer patient, (e) urine, and (f) blood. The aforementioned tissues can also be corrected by biopsy. When the collected tissues are subjected to immunohistological staining, they can be embedded in paraffin or can be frozen before use.

The monoclonal antibody of the present invention capable of specifically recognizing ROBO1 existing on the surface of a cell can be labeled with a radioactive metal, and it can thereby be used as a tumor diagnostic agent used in PET. An example of such a radioactive metal used herein is $^{64}$Cu, but examples are not limited thereto. Of these, $^{64}$Cu is preferable.

The monoclonal antibody of the present invention that has been labeled with a radioactive metal can be mixed with, dissolved in, or emulsified in a pharmaceutically acceptable carrier, and as a result, it can be used as a tumor diagnostic agent used in PET. For example, together with a pharmaceutically acceptable solvent, excipient, binder, stabilizer, dispersant, and other agents, the radioactive metal-labeled monoclonal antibody of the present invention can be processed into a dosage form such as an injection solution, a suspension, or an emulsion. In order to produce an injection solution, the radioactive metal-labeled monoclonal antibody of the present invention can be dissolved in an aqueous solution, and preferably in a Hanks' solution, a Ringer's solution, or a physiologically compatible buffer solution such as a physiological saline buffer. Moreover, the composition can adopt the form of a suspension, a solution, an emulsion, etc., in an oily or watery vehicle.

The administration route of a tumor diagnostic agent used in PET is not particularly limited. In general, such a tumor diagnostic agent can be administered via a parenteral administration route, and it can be administered in the form of an injection (subcutaneous injection, intravenous injection, intramuscular injection, intraperitoneal injection, etc.), or through the skin or mucosa, for example.

The dosage and the number of doses are different depending on the age of a patient, the body weight of a patient, the purpose of diagnosis, etc. In general, the monoclonal antibody of the present invention can be administered within the range between approximately 0.1 mg and 1,000 mg, and preferably between approximately 0.1 mg and 100 mg, per single administration per kg of body weight.

EXAMPLES

The present invention will be described more in detail below. However, these examples are not intended to limit the scope of the present invention.

Example 1

Production of anti-ROBO1 Monoclonal Antibody (A) Method (1) Isolation of ROBO1 cDNA The cDNA of ROBO1 was isolated by the following method. Single stranded cDNA was prepared from Alexander cells. The prepared single stranded cDNA was used as a template, and amplification was carried out by the PCR method using the following two primers: RBV2F-TA (5'-ACCATGATTGCGGAGCCCGCTCAC-3' (SEQ ID NO: 1)) and RBR-TA (5'-GCTTTCAGOTTCCTCTAATTC-3' (SEQ ID NO: 2)). The primer RBV2F-TA was designed such that it would hybridize with the 5'-terminus of a ROBO1 gene (GenBank: NM_133631). On the other hand, the primer RBR-TA was designed such that it would hybridize with the 3'-terminus thereof. In the PCR method, a reaction solution was prepared in accordance with the protocols of a LA-PCR kit (manufactured by TAKARA). A primary denaturation was first carried out at 95° C. for 2 minutes. Thereafter, a cycle consisting of 94° C.-15 seconds, 63° C.-15 seconds and 72° C.-5 minutes was repeated 30 times. Finally, an elongation reaction was carried out at 72° C. for 10 minutes. Subsequently, a band of approximately 5 kbp corresponding to an estimated ROBO1 sequence was detected by agarose gel electrophoresis. Such a specific amplified fragment was inserted into pcDNA3.1/V5-His TOPO (manufactured by Invitrogen) by the TA cloning method. As a result of confirming the nucleotide sequence by a common method, it became clear that the isolated cDNA was ROBO1 (ROBO1/pcDNA3.1).

(2) Production of gp64-bound recombinant baculovirus, in which ROBO1 extracellular region domain is expressed As shown in FIG. 1, five types of antigens including a region comprising the initial immunoglobulin region (Ig1) were designed from the N-terminus of ROBO1, and such antigens were allowed to express in the forms of fusion proteins with the membrane protein pg64 of baculovirus. That is to say, using the primer sets as described below, and also using the aforementioned ROBO1 cDNA as a template, a gene encoding each region of ROBO1 was amplified by the PCR method, and the thus amplified product was then inserted into a pGEM-Te vector (manufactured by Promega). The nucleotide sequence was confirmed by a common method. Thereafter, a gene fragment cleaved with the restriction enzyme KpnI was inserted into a pBacSurf vector (manufactured by Novagen), so as to construct transfer vectors ROBO1N/pBS, gp1/pBS, gp2/pBS, gp3/pBS, and gp4/pBS. Subsequently, 4 μg of each vector was cleaved with the restriction enzyme BpII (manufactured by Fermentas) so as to create a straight chain. The vector was then introduced together with Bac-N-Blue DNA into Sf9 cells in accordance with the instructions of Invitrogen, so as to prepare a fusion protein-expressing recombinant baculovirus consisting of each ROBO1 domain (Ig1, Ig2, Ig3, Fn1, or Fn3) and gp64.

The thus prepared recombinant virus was added to Sf9 cells ($2 \times 10^6$ cells/ml) such that MOI became 5, so that the aforementioned cells became infected with the aforementioned recombinant virus. Thereafter, the infected cells were cultured at 27° C. for 3 days. After the culture has been carried out for 3 days, a budded baculovirus (BV) that expressed a fusion protein consisting of each ROBO1 domain and gp64 was recovered from the culture supernatant. That is to say, the culture solution was centrifuged at 1,500×g for 15 minutes, so as to eliminate cells and cell disintegrated products. The recovered culture supernatant was then centrifuged at 45,000×g for 30 minutes. The obtained precipitate was suspended in PBS, and the suspension was further centrifuged at 1,500×g, so as to eliminate cell components. The supernatant was again centrifuged at 45,000×g, and the obtained precipitate was then suspended in PBS. The thus obtained fraction was defined as a BV fraction, which was then used as an antigen in immunization.

All protein concentrations were assayed using a DC protein assay kit (Bio-rad) obtained by modification of the Lowry method. Bovine serum albumin (BSA) was used as a standard of protein assay.

```
Primer sets
                                              (SEQ ID NO: 3)
ROBO1N-F:  5'-GGTACCCCTTCGTCAGGAAGATTTTCCAC-3'

(SEQ ID NO: 4)
ROBO1N-R:  5'-GGTACCGAGTAATTCCTTGCTACACA-3'

(SEQ ID NO: 5)
Gp1-F:     5'-GGTACCCGATGAAGGAGTCTATGTCTGTGT-3'

(SEQ ID NO: 6)
Gp1-R:     5'-GGTACCGCACCAACACAAACATATTTGCCA-3'

(SEQ ID NO: 7)
Gp2-F:     5'-GGTACCCACCAATATGGTTGGGGAACGTGA-3'

(SEQ ID NO: 8)
Gp-2-R:    5'-GGTACCGCAGATGCTTCAGCTTTGCCCACC-3'

(SEQ ID NO: 9)
Gp3-F:     5'-GGTACCCGCTAATGCATATGGAATTAGTGA-3'

(SEQ ID NO: 10)
Gp3-R:     5'-GGTACCGCATTCTTGGATACAGTTACACCT-3'

(SEQ ID NO: 11)
Gp4-F:     5'-GGTACCCGCACCCAGTGCCCCACCCCAAGG-3'

(SEQ ID NO: 12)
Gp4-R:     5'-GGTACCGCATCTGAAATCTGCTGAGCGAGG-3'
```

(3) Production of full-length ROBO1-expressing virus

The ROBO1 cDNA comprising the fill-length ORF region described in (1) above was directly inserted into a pBlueBac4.5-TOPO vector, and the sequence was then analyzed. Thereafter, a transfer vector ROBO1/pBB having a correct nucleotide sequence was produced. Using 4 Mg of ROBO1/pBB, a recombinant baculovirus was produced in the same above manner. A BV fraction was prepared in the same manner as described in (2) above, and it was used as an antigen in immunization.

(4) Detection of recombinant antigen by western blot method

In order to confirm expression of various types of the prepared BV antigens, detection was carried out by the Western blot analysis. Each of the aforementioned BV antigens was subjected to SDS-polyacrylamide gel electrophoresis, so as to separate a protein, followed by transcription on Hybond-P (manufactured by Amersham Biosciences). An anti-gp64 antibody (Tanaka T. et al., J Atheroscler Thrombo, 9: 233-242, 2002) was diluted by a factor of 50,000, and it was used as a primarily antibody. As a secondary antibody, an HRP-labeled anti-mouse IgG antibody (manufactured by the Jackson Laboratory) was used. Detection was carried out using ECL plus (manufactured by Amersham Biosciences).

(5) Production of recombinant soluble-type ROBO1 (sROBO1-His)

Soluble-type ROBO1 (sROBO1-His) formed by adding a His tag to the C-terminus of the extracellular region of ROBO1 was produced as follows, and it was used as an antigen in ELISA during the screening of an antibody.

The ROBO1 cDNA described in (1) above was used as a template, and a gene encoding the extracellular region was amplified by the PCR method using the primer RBV2F-TA (5'-ACCATGATTGCGGAGCCCGCTCAC-3' (SEQ ID NO: 13) and the primer RB_SH_TA (5'-GGCCGGCTGCT-TCACCACAT-3' (SEQ ID NO: 14). The PCR product was directly inserted into a pBlueBac4.5-TOPO vector, and the sequence was then analyzed. Thereafter, a transfer vector ROBO1/pBB having a correct nucleotide sequence was produced. Using 4 μg of ROBO1/pBB, a recombinant baculovirus was produced in the same above manner.

Subsequently, sROBO1-His was prepared as follows. That is, sf9 cells having a concentration of $2 \times 10^6$/ml were infected with sROBO1-His-expressing recombinant baculoviruses, such that MOI became 5. The thus infected cells were cultured at 27° C. for 3 days. Thereafter, the culture supernatant was recovered. The sROBO1-His contained in the culture supernatant was purified using Ni-NTA superflow (QIAGEN) in accordance with protocols included with the kit. The purified product was concentrated using Centricon-10 (manufactured by Amicon), and the buffer was substituted with PBS, so as to prepare sROBO1-His.

(6) Establishment of ROBO1 constant expression cell line

1 μg of the ROBO1/pcDNA3.1 produced in (1) above was introduced into $2 \times 10^5$ HEK293 cells (a 6-well plate was used), using 3 μl of FuGene6 reagent (manufactured by Roche Diagnostics). Three days after introduction of the expression vector, the medium was exchanged with a fresh one. Neomycin (Geneticin; GIBCO) was added in a concentration of 500 μg/ml to DMEM+10% FCS, and drug selection was carried out using neomycin. Such drug selection was carried out for 1 month, so as to carry out the monocloning of ROBO1-expressing HEK293 cells.

(7) Production of Anti-ROBO1 monoclonal antibody (BV antigen)

ROBO1-N (Ig1), gp1 (g2), gp2 (Ig3), and gp4 (Fn3), which were the BV antigens prepared in (2) above, and full-length expression type BV (ROBO1-Full), were used as antigens to produce anti-ROBO1 monoclonal antibodies. That is, each BV antigen corresponding to 1 mg of protein suspended in PBS was mixed with 200 ng of pertussis toxin, and the mixture was then injected into the subcutis of a gp64 transgenic mouse (WO03/104453) for the initial immunization. Such a gp64 excessive expression transgenic mouse is a mouse in which gp64 has been allowed to systemically express using a pCAGGS vector.

For the subsequent immunization, only the BV antigen corresponding to 500 μg of protein was injected into the subcutis of the aforementioned mouse. For the final immunization, 250 μg of each BV antigen was injected into the vein of the aforementioned mouse. Three days after the final immunization, splenic cells were isolated from the mouse, and the thus isolated splenic cells were then fused with mouse P3U1 cells according to a common method, so as to establish a hybridoma cell line. Such hybridomas were selected with each screening system including the following ELISA as a typical example.

Each monoclonal antibody was prepared from the culture supernatant of the generated hybridoma cells according to the ammonium sulfate precipitation method. In addition, the isotype of a mouse antibody was identified using Mouse Monoclonal Antibody Isotyping Test Kit MMT1 (manufactured by Serotec; distributed by Dainippon Pharmaceutical Co.).

(8) ELISA Screening of hybridoma supernatant

Hybridoma cells that produced anti-ROBO1 monoclonal antibodies were selected by ELISA in which sROBO1-His had been immobilized. In the ELISA method, 50 µl (5 µg/ml) of sROBO1-His was left on a 96-well flat plate (manufactured by Falcon) at 4° C. over day and night. Thereafter, the resultant was blocked in a TBS buffer that contained a 40% Block-Ace reagent (Dainippon Pharmaceutical Co.), and a hybridoma culture supernatant was added thereto, followed by a reaction at room temperature for 1 hour. Subsequently, an HRP-labeled anti-mouse IgG antibody (manufactured by Jackson) was allowed to react with the reaction product at room temperature for 1 hour. The resultant was washed 4 times, and it was then allowed to react with a 3,3',5,5'-etramethylbenzidine (I) reagent (manufactured by Sigma) at room temperature for 1 hour. The reaction was terminated with 0.5 N sulfuric acid, and the absorbance at 491 nm was measured with a microplate reader MultickanJX (manufactured by Labsystems).

In addition, in the case of immunization with a BV antigen, 50 µl of BV antigen (50 µg/ml) used as an immunogen was left on a 96-well flat plate (manufactured by Falcon) at 4° C. over day and night, so that it became immobilized thereon. Thereafter, the ELISA assay was carried out in the same above manner. Wild-type BV was used as a control.

(9) FACS screening of hybridoma supernatant

In order to screen an antibody that recognizes a steric structure, a hybridoma supernatant was screened by FACS analysis. That is, ROBO1-forced expression HEK293 cells or HEK293 cells used as negative controls were suspended in a FACS solution (1% albumin and 0.1% $NaN_3$ in PBS). Thereafter, 10 µl of hybridoma supernatant was added to the cell suspension, and the obtained mixture was then allowed to react at 4° C. for 60 minutes. Thereafter, the reaction solution was washed with a FACS solution twice, and a FITC-labeled anti-mouse IgG antibody (manufactured by Jackson) was added thereto. The obtained mixture was allowed to react at 4° C. for 30 minutes. Thereafter, the resultant was washed with a FACS solution twice, and the FACS analysis was then carried out using FACSCalibur (manufactured by Becton Dickinson) in accordance with instructions for use.

(10) FMAT 8200 CDS screening

FMAT 8200 CDS, which was based on Cell ELISA, was used to screen a hybridoma supernatant. That is, $1 \times 10^4$ ROBO1-expressing HEK293 cells were cultured on a 96-well Black plate used for FMAT assay over day and night, and on the following day, the buffer was exchanged with 100 µl of assay buffer (1% BSA+0.01% azide/PBS). Thereafter, 10 µl of hybridoma supernatant and 50 µl of FMAT Blue-labeled anti-mouse IgG antibody (final concentration: 1 µg/ml; Applied Biosystems) were added to each well, and it was then left at rest at room temperature in a dark room for 2 hours. Thereafter, detection was conducted with 8200 CDS. The fluorescence intensity ratio was compared with that of a negative control (without supernatant), and positive determination was carried out.

(11) Production of anti-ROBO1 monoclonal antibody (sROBO1-His antigen)

The sROBO1-His prepared in (5) above was used as an antigen to produce an anti-ROBO1 monoclonal antibody. That is, an sROBO1-His antigen corresponding to 100 µg of protein suspended in PBS was mixed with 200 ng of pertussis toxin, and the mixture was then injected into the subcutis of an MRL/lpr mouse that was an autoimmune disease mouse for the initial immunization. For the subsequent immunization, an sROBO1-His antigen corresponding to 50 µg of protein was injected into the subcutis of the aforementioned mouse 4 to 6 times. For the final immunization, 50 µg of sROBO1-His antigen was injected into the vein of the aforementioned mouse. Three days after the final immunization, splenic cells were isolated from the mouse, and the thus isolated splenic cells were then fused with mouse P3U1 cells by a conventional method, so as to establish a hybridoma cell line.

Subsequently, screening was carried out by the same above-described method.

(B) Results (1) Cloning of ROBO1 and production of expression vector

ROBO1 cDNA was amplified by PCP An animal cell expression vector ROBO1/pcDNA3.1 and an insect cell expression transfer vector ROBO1/pBB were produced. V5 and a His6 tag were added to the C-terminus of each of the two vectors, respectively. In addition, there was produced a transfer vector sROBO1/pBB used in expression of soluble-type ROBO1 (1-862 amino acids, sROBO1-His) that was cleaved on the N-terminal side of a transmembrane region.

As shown in FIG. 1, 5 types of gp64-bound antigens, including a region comprising the initial immunoglobulin region (Ig1) from the N-terminus of ROBO1 as a typical example, were designed. At the final stage, a sequence comprising each domain of interest was inserted into a pBacSurf vector (manufactured by Novagen), so as to construct transfer vectors ROBO1N/pBS, gp1/pBS, gp2/pBS, gp3/pBS, and gp4/pBS.

The cDNA sequence of ROBO1 differs from the sequence registered at GenBank, and VGS was inserted into a certain site after the amino acid at position 309 after the third immunoglobulin domain (FIG. 2). It is considered that this was caused by mutation in Alexander cells used as a template. Insertion of 3 amino acids was observed in all cDNA cloned from the cDNA portions of fetal liver, fetal brain, HuH6, etc.

(2) Confirmation of expression of antigenic protein

Various types of recombinant viruses were constructed as antigens used in immunization. Thereafter, each expression was confirmed by the Western blot analysis. As a result, as shown in FIGS. 3A and 3B, it was found that ROBO1N_BV, gp1_BV, gp2_BV, and gp4_BV were all successfully expressed. However, expression of gp3 encoding the third position of an immunoglobulin domain was not confirmed (FIG. 3A). Thus, hereafter, pg3 was excluded from immunogens.

ROBO1-Full_BV, wherein not a gp64-bound type but full-length ROBO1 was allowed to express, is shown in FIG. 3B. Moreover, with regard to sROBO1-His, fractions 2 and 3 as shown in FIG. 4, which had been purified with a Ni-NTA column, were combined, so as to produce a purified product.

(3) Production of ROBO1 constant expression HEK293 cells

ROBO1/pcDNA3.1 was used to establish ROBO1 constant expression cells. 1 µg of ROBO1/pcDNA3.1 was introduced into $2 \times 10^5$ HEK293 cells, using 3 µl of FuGene6 reagent (manufactured by Roche Diagnostics). Two days later, neomycin (500 µg/ml, Geneticin, GIBCO) was added to the medium, and further 1 week later, selection was carried out by 1 cell/well limiting dilution. Thereafter, the monocloned cells, which had acquired ability to tolerate neomycin, were recovered, and each RIPA lysate solution was prepared. 2 µg (equal amount) of the lysate solution corresponding to protein amount was supplied to each lane, and the Western blot analysis was then carried out (FIG. 5). Using, as an indicator, a band probably indicating the molecular weight of ROBO1 detected using A7241A as an anti-ROBO1 monoclonal antibody, an anti-V5 antibody, etc., a comparison was made. As a result, it was revealed that expression of ROBO1 in R#6, R#10 and R#12 was higher than in the case of other clones.

Continuously, FACS analysis was carried out using an anti-V5 antibody. Since a V5 tag was added to the C-terminus of the intracellular region of ROBO1, a FACS solution that contained 0.1% saponin was used during addition of a primary antibody, such that the antibody could detect the V5 tag in cells. As a result, no shifts were observed in the HEK293 cells used as a control, whereas a specific peak shift to the V5 antibody was observed in the case of the ROBO1-expressing cell lines R#6, R#10 and R#12 (FIG. 5). As a result of the aforementioned analysis, R#6, the expression level of which was highest in the comparison performed in the Western blot analysis, was defined as a ROBO1-expressing HEK293 cell line.

(4) Production of anti-ROBO1 monoclonal antibody

As shown in Table 1, various types of antigens were combined with a mouse to produce a large number of anti-ROBO1 monoclonal antibodies.

TABLE 2

| Antibody | Antigen | Subclass | Lot |
|---|---|---|---|
| A7241A | ROBO1N | IgG1 | A-1 |
| B0701A | sROBO1-His | IgG1 | A-1 |
| B1511A | sROBO1-His | IgM | A-1 |
| B2220A | ROBO1gp4 | IgG2a | A-1 |
| B2212A | ROBO1gp4 | IgG2a | A-1 |
| B2318C | ROBO1gp4 | IgG2a | A-2 |
| B2542A | ROBO1gp2 | IgG3 | A-1 |
| B2610A | ROBO1gp4 | IgG1 | A-1 |
| B2613A | ROBO1gp4 | IgG2a | A-1 |
| B2701A | ROBO1gp4 | IgG2a | A-1 |
| B2706A | ROBO1gp4 | IgG2a | A-1 |
| B2711A | ROBO1gp4 | IgG2a | A-1 |
| B4704A | ROBO1-Full | IgG2a | A-1 |
| B5202A | ROBO1-Full | IgG2a | A-1 |
| B5209B | ROBO1-Full | IgG2b | A-1 |
| B5303A | ROBO1-Full | IgG2a | A-1 |
| B5303C | ROBO1-Full | IgG2a | A-1 |
| B5304A | ROBO1-Full | IgG2b | A-1 |
| B5309D | ROBO1-Full | IgG2a | A-1 |
| B5310C | ROBO1-Full | IgG1 | A-1 |
| B5315C | ROBO1-Full | IgG2a | A-1 |
| B5317B | ROBO1-Full | IgG2b | A-1 |

TABLE 1

| Code No. | Immunization antigen | Mouse | n | CD40L | Hybridoma serum concentration | Screening number (Well) |
|---|---|---|---|---|---|---|
| A7200 | ROBO1N_BV | gp64TGM | 2 | — | 15% FCS | 1248 |
| B0700 | sROBO1 | MRL/lpr | 1 | — | 15% FCS | 864 |
| B1500/B1600 | sROBO1 | MRL/lpr | 2 | — | CS. SFM | 1369 |
| B2200 | gp4_BV | gp64TGM + CCR5(+/−) | 1 | — | 15% FCS | 468 |
| B2300 | gp4_BV | gp64TGM + CCR5(+/−) | 1 | CD40L_BV | 15% FCS | 492 |
| B2400 | gp1_BV | gp64TGM + CCR5(+/−) | 1 | — | 15% FCS | 548 |
| B2500 | gp2_BV | gp64TGM + CCR5(+/−) | 1 | — | 15% FCS | 460 |
| B2600 | gp4_BV | gp64TGM + CCR5(+/−) | 1 | — | 15% FCS | 777 |
| B2700 | gp4_BV | gp64TGM + CCR5(+/−) | 1 | CD40L_BV | 15% FCS | 444 |
| B4700 | ROBO1_Full_BV | gp64TGM | 2 | CD40L_BV | 15% FCS | 1039 |
| B5200 | ROBO1_Full_BV | gp64TGM | 1 | CD40L_BV | 10% CS | 185 |
| B5300 | ROBO1_Full_BV | gp64TGM | 1 | — | 10% CS | 444 |

| Code No. | FACS positive | WB positive | Antibody obtained | Screening method |
|---|---|---|---|---|
| A7200 | — | 1 | A7241A | BV_ELISA |
| B0700 | 1 | 0 | B0701A | ELISA, WB, FACS(HepG2) |
| B1500/B1600 | 3 | 1 | B1511A | ELISA, WB, FACS(HepG2) |
| B2200 | 26 | 16 | B2212A | ELISA, WB, FACS |
| B2300 | 1 | 1 | B2318D | ELISA, WB, FACS |
| B2400 | 0 | 9 | B2424A | ELISA, WB, FACS |
| B2500 | 0 | 30 | B2511A, B2518, B2542A | ELISA, WB, FACS |
| B2600 | 2 | 6 | B2610A, B2613A B2701A, B2706A, | ELISA, WB, FACS |
| B2700 | 1 | 4 | B2711A | ELISA, WB, FACS |
| B4700 | 2 | 4 | B4704A, B4717A | ELISA, WB, FACS |
| B5200 | 2 | — | B5202A, B5209B | ELISA, WB, FACS, FMAT |
| B5300 | 13 | — | B5303A, B5303C, B5304A, B5309D, B5310C, B5315C, B5317B | ELISA, WB, FACS, FMAT |

*: HepG2 was used for FACS screening of B0700 and B1500 series
*: ROBO1-expressing HEK293 cell was used for FACS screening of B2200 and the subsequent.

As a screening system, purified antigen ELISA and BV antigen ELISA had been performed from the beginning. FACS screening was performed after B2200 series, and FMAT 8200 CDS screening was performed after B5200 series. As a result, as shown in Table 2, various types of anti-ROBO1 monoclonal antibodies were successfully produced.

A hybridoma that produces the monoclonal antibody B5209B was deposited with the National Institute of Advanced Industrial Science and Technology, an Independent Administrative Institution under the Ministry of Economy, Trade and Industry, at the AIST Tsukuba (Central 6, Higashi 1-1-1, Tsukuba, Ibaraki, Japan (postal code number: 305-8566)) under accession No. FERM P-21238 on Mar. 2, 2007, and was transferred to an international deposition on Oct. 16, 2007 under accession No. FERM BP-10921. All restrictions upon public access to the deposited material will be irrevocably removed upon the grant of a patent on this application.

(C) Consideration

Since human ROBO1 showed extremely high amino acid sequence homology of 95% or more with a mouse, and since an epitope portion of interest was an extracellular region, with regard to production of an antibody, a method of obtaining such an antibody was devised. That is to say, two types of methods, namely, a method of immunizing a gp64 expression transgenic mouse with a BV antigen and a method of immunizing an MRL/lpr mouse with a soluble-type ROBO1 purified antigen (sROBO1-His) were applied in the present studies.

In order to enhance the antigenecity of an immunogen, a BV antigen is used in the form of a virus for immunization. However, in such a case, large quantities of antibodies reacting with gp64 that is a main component of the virus may possibly be produced. Thus, in the present invention, gp64 excessive expression transgenic mice were used, and an attempt was made to obtain large quantities of antibodies reacting with antigens of interest.

Moreover, to date, MRL/lpr mice have been widely studied as models of systemic autoimmune diseases such as human lupus nephritis, polyarteritis nodosa, rheumatoid arthritis, or Sjogren's syndrome. We expected that an antibody more unique than that obtained from a common mouse could be obtained, when such autoimmune disease mice were immunized with ROBO1 that was predicted to have low antigenecity. Thus, we selected this method.

As a result of performing the two above strategies, as shown in Table 2, a great number of anti-ROBO1 monoclonal antibodies, including antibodies that recognized a steric structure, were successfully produced. A simple comparison could not be made between the two methods because different immunogens were used in such methods. However, when compared with other types of mice, MRL/lpr mice were greatly damaged during immunization. Thus, the MRL/lpr mice required careful handling.

The number of positive clones was largely different depending on the type of screening. The used immunogen was considered to be one of the factors. At least, acquisition of a FACS positive antibody reacting with an immunoglobulin domain has not yet been confirmed so far. This region is a ROBO1 ligand-binding region, and the highest homology was conserved in this region regardless of species. Thus, it was anticipated that this became immunologically tolerant, and therefore it was considered difficult to produce such an antibody. Moreover, there was a possibility that that a ROBO1-like protein contained in bovine serum reacted as an absorption component when an anti-ROBO1 antibody was screened. Thus, it was predicted that antibodies that well recognized a steric structure failed to be screened.

As another factor, there was a possibility that the steric structure of a gp64-bound antigen used as an antigen differed from that of ROBO1. An S—S bond exists in each immunoglobulin domain. There was a possibility that such an S—S bond was not reconstructed when it was fused with gp64. In reality, Cys considered to be necessary for reconstruction was conserved in each immunoglobulin domain and was used for designing. However, it was also considered that it was influenced by the structure of gp64.

For the aforementioned reasons, the following two creative efforts were made in production of antibodies in B52 and 53 series. That is, CS having a few bovine ROBO1-like proteins in serum was used instead of FBS in the screening of hybridomas, and a ROBO1-Full/BV antigen, wherein the steric structure of an immunoglobulin domain was possibly maintained, was used as an immunogen. As a result, the number of FACS positive antibodies established was clearly increased (Tables 1 and 2). In the present invention, using this system, an antibody exhibiting high cytotoxicity was successfully isolated in the last result.

Example 2

Characterization of Anti-ROBO1 Monoclonal Antibody using Cytotoxicity (CDC Activity) as Indicator (A) Method (1) FACS analysis of anti-ROBO1 monoclonal antibody An anti-ROBO1 monoclonal antibody was analyzed in accordance with the method described in the "FACS screening of hybridoma supernatant" section in Example 1. The fluorescence intensity was converted to numbers (X mean) and then used.

(2) Measurement of CDC activity of anti-ROBO1 monoclonal antibody

Calcein (Wako)-labeled ROBO1-expressing HEK293 cells were used in analysis. Specific operations are as follows.

(i) Production of human albumin veronal buffer (HAVB)

12.75 g of NaCl (highest quality; Wako Pure Chemical Industries, Ltd.), 0.5625 g of Na-barbital (highest quality; Wako Pure Chemical Industries, Ltd.), and 0.8625 g of barbital (highest quality; Wako Pure Chemical Industries, Ltd.) were dissolved in Milli-Q water, resulting in a volume of 200 ml. The obtained solution was then subjected to an autoclave treatment (121° C., 20 minutes). Thereafter, 100 ml of warm Milli-Q water, which had been treated with an autoclave, was added to the resultant solution. The pH of the solution was found to be pH 7.43 (recommended pH: 7.5). The thus obtained solution was defined as a 5× veronal buffer. 0.2205 g of $CaCl_2.2H_2O$ (highest quality; Junsei Chemical Co., Ltd.) was dissolved in 50 ml of Milli-Q water, resulting in a concentration of 0.03 mol/l, and the obtained solution was defined as a CaCl solution. 1.0165 g of $MgCl_2.6H_2O$ (highest quality; Junsei Chemical Co., Ltd.) was dissolved in 50 ml of Milli-Q water, resulting in a concentration of 0.1 mol/l, and the obtained solution was defined as an $MgC_2$ solution. 100 ml of 5× veronal buffer, 4 ml of human serum albumin (Buminate (registered trademark) 25%, 250 mg/ml human serum albumin; Baxter), 2.5 ml of $CaCl_2$ solution, 2.5 ml of $MgCl_2$ solution, 0.1 g of KCl (highest quality; Junsei Chemical Co., Ltd.), and 0.5 g of glucose (D(+)-glucose; anhydrous glucose; highest quality; Wako Pure Chemical Industries, Ltd.) were dissolved in Milli-Q water, resulting in a volume of 500 ml. The obtained solution was defined as HAVB. HAVB was filtrated and sterilized, and it was then conserved at a preset temperature of 5° C.

(ii) Preparation of target cells

ROBO1 forced expression HEK293 cells and ALX were cultured in DMEM medium/10% FBS (SIGMA) (0.5 mg/ml neomycin (Geneticin, GIBCO) was added to ROBO1-expressing HEK293 cells). Thereafter, the cells were removed from the dish using a cell desquamation buffer (GIBCO). The cells were then poured into each well of a 96-well U bottom plate (BECTON DICKINSON) in a concentration of $1 \times 10^4$ cells/well, and they were then cultured overnight. After completion of the culture, 5.55 MBq of chrome-51 or a calcein reagent (Wako) having a final concentration of 20 μg/ml was added to the culture, and the obtained mixture was then cultured in a 5% carbon dioxide incubator at 37° C. for 1 hour. The resultant cells were washed with HAVB twice, and 50 μl of HAVB was added thereto to produce target cells.

(iii) Preparation of baby rabbit complement 1 vial of baby rabbit complement (Cedarlane) was dissolved in 1 ml of distilled water used for injection (Fuso Pharmaceutical Industries, Ltd.) so as to prepare a complement solution (a complement itself was prepared before use for a test).

(iv) Measurement of CDC activity

An anti-ROBO1 monoclonal antibody was diluted with HAVB so as to prepare an antibody solution, and 50 μl each of such an antibody solution was added to target cells. The obtained mixture was left at rest on ice for 15 minutes (final concentration: 0.16 μg/ml to 100 μg/ml). Subsequently, a complement solution was added in a concentration of 100 μg/ml to each well (final concentration: 5% to 25%). The obtained mixture was left at rest in a 5% carbon dioxide incubator at 37° C. for 90 minutes. The plate was centrifuged, and 100 μl each of supernatant was then recovered from each well. Thereafter, the radioactivity thereof was measured using a gamma counter (measured at 494 nm in the case of calcein labeling). A specific chrome release rate was obtained using the following formula:

Specific chrome release rate(%)=$(A-C)/(B-C) \times 100$

A indicates radioactivity (cpm) in each well; B indicates the mean value of radioactivity (cpm) in a well, wherein 100 μl of 2% NP-40 aqueous solution (Nonidet P-40, Nacalai Tesque, Inc.) and 50 μl of HAVB were added to target cells; and C indicates the mean value of radioactivity (cpm) in a well, wherein 150 μl of HAVB was added to target cells. The test was carried out in a triple manner, and the mean value and standard deviation of CDC activity (%) were calculated.

(3) Epitope analysis of anti-ROBO1 monoclonal antibody

ROBO1 has 5 immunoglobulin domains and 3 fibronectin III domains in the extracellular region thereof. Thus, antigens used in epitope analysis were designed such that they were overlapped each other, and they were allowed to express as GST-bound recombinants (FIG. 6). In addition to the 8 antigens, 30 amino acids located upstream of a transmembrane region (UT1_GST, 831-860 amino acids), Ig2-3 obtained by combining the second immunoglobulin domain with the third immunoglobulin domain, and Ig4-5 obtained by combining the fourth immunoglobulin domain with the fifth immunoglobulin domain, were prepared (total 11 types). That is to say, using the primer sets as described below, a gene fragment of interest was cloned by the PCR method, and it was then inserted into the BamHI-HindIII site of a pET41b vector (total 11 vectors ranging from Ig1/pET41b to UT1/pET41b). BL21 (DE3) (Novagen) was transformed with each expression vector. A cell mass whose expression had been induced in 0.5 M IPTG at 37° C. for 3 hours was disintegrated with ultrasonic wave using 1% Triton X-100/PBS. The thus obtained insoluble fraction and soluble fraction were used as antigens in epitope analysis. In addition, sROBO1-His used as an immunogen was used herein as a control full-length extracellular region.

```
                                       (SEQ ID NO: 15)
Ig1F:  5'-GGATCCGATGATTGCGGAGCCCGCTCACTTTTACC-3'

(SEQ ID NO: 16)
Ig1R:  5'-AAGCTTGACATCCGAAGGGTTTTGTCTGAAGTCAT-3'

(SEQ ID NO: 17)
Ig2F:  5'-GGATCCGAATGCATCGCTGGAAGTAGCCATACTTC-3'

(SEQ ID NO: 18)
Ig2R:  5'-AAGCTTACTGGGTCTCTTCACAAATGATGGTCTC-3'

(SEQ ID NO: 19)
Ig3F:  5'-GGATCCGGAGAGTGAAGTAGCCGAGCTGACTGTC-3'

(SEQ ID NO: 20)
Ig3R:  5'-AAGCTTCCGTCCCAAAGCAACAACCTGGTCACGG-3'

(SEQ ID NO: 21)
Ig4F:  5'-GGATCCGCCCCGTGACCAGGTTGTTGCTTTG-3'

(SEQ ID NO: 22)
Ig4R:  5'-AAGCTTTACAGTCTGATTCACAGGACCTTGTCG-3'

(SEQ ID NO: 23)
Ig5F:  5'-GGATCCGATCATCACAAAGGCATATTTGGAAG-3'

(SEQ ID NO: 24)
Ig5R:  5'-AAGCTTTGTATTTCTGCTGACATCTGTCACTTC-3'

(SEQ ID NO: 25)
Fn1F:  5'-GGATCCGCCAAATTTAATCCCTAGTGCCCCATC-3'

(SEQ ID NO: 26)
Fn1R:  5'-AAGCTTAAGGACGGTGGGGTTGTGGAGGTGCAG-3'

(SEQ ID NO: 27)
Fn2F:  5'-GGATCCGAAGCAGGTCCAGAGAGAGCTGGGAAATG-3'

(SEQ ID NO: 28)
Fn2R:  5'-AAGCTTCTTGGATACAGTTACACCTTGGGGTGG-3'

(SEQ ID NO: 29)
Fn3F:  5'-GGATCCGTTTGCCAAAACCCTGGAAGAAGCACC-3'

(SEQ ID NO: 30)
Fn3R:  5'-AGCTTCTGCTTCACCACATCTGAAATCTGCTG-3'

(SEQ ID NO: 31)
UT1F:  5'-GGATCCGCAGTTCATCCAGCTGGATGCC-3'

(SEQ ID NO: 32)
UT1R:  5'-AAGCTTCTGCTTCACCACATCTGAAATCTGCTG-3'
* Ig2-3 indicates the combination of an Ig2F primer with an Ig3R
primer; and Ig4-5 indicates the combination of an Ig4F primer
with an Ig5R primer.
```

(B) Results (1) FACS analytical comparison among anti-ROBO1 monoclonal antibodies reacting with ROBO1-expressing HEK293 cells Using a B2318C antibody (IgG2a) as an indicator, B1511A (IgM) and B2610A (IgG1) were subjected to volume-dependent FACS affinity analysis (FIG. 7A). The affinity of B2318C for ROBO1 in a low antibody concentration tended to be lower than that in the case of other antibodies. Continuously, the antibody concentration was set at 2 μg/ml, and antibodies produced in B47, B52 and B53 series as ROBO1-Full_BV/gp64TGM immunity series (Table 1) were subjected to FACS analysis (FIG. 7B). The concentration-dependent curves of main antibodies are shown in FIG. 7C. From the aforementioned analysis, it became clear that a large number of antibodies exhibiting high affinity for ROBO1 on the cell surface are contained in the B47, B52 and B53 series.

(2) Comparison of CDC activities of anti-ROBO1 monoclonal antibodies

The antibody volume-dependent CDC activities of B2318C, B1511A and B2610A were evaluated (FIG. 8A). The same tendency as that in the FACS analysis as shown in FIG. 7A was obtained also in the measurement of such CDC activities. It became clear that B1511A and B2610A had cytotoxicity at a low volume, when compared with B2318C.

Considering the aforementioned analytical results, the CDC activity of an anti-ROBO1 monoclonal antibody in a concentration of 0.1 µg/ml was compared with that in a concentration of 1.0 µg/ml (FIG. 9). As a result, it was demonstrated that B5209B, B5303A and B5317B had activities stronger than any antibodies that had previously been obtained. Continuously, a comparison was made among the aforementioned antibodies and the B2318 antibody in terms Subsequently, antibodies obtained in the B47, B52 and B53 series obtained by immunization of gp64TGM with a ROBO1-Full_BV antigen were subjected to epitope analysis using each GST antigen. As a representative example of the results of the Western blot analysis, a blot view of the B5317B antibody is shown in FIG. 11B. Finally, the binding domains of all the antibodies were identified. The results are summarized in Table 3. As a result of the immunization with ROBO1-Full_BV, there was a possibility that an antibody binding to any portion of an extracellular region was obtained. However, as a result, all antibodies other than the first fibronectin III domain of B5304A bound to the fifth immunoglobulin domain. Moreover, it was also found that the binding site of B1511 A (IgM) obtained by immunization of an MRL/lpr mouse with sROBO1-His was also the fifth immunoglobulin domain.

TABLE 3

| Antibody | Antigen | Binding region | Subclass | Lot | WB | FACS (nM) | CDC (%) |
|---|---|---|---|---|---|---|---|
| A7241A | ROBO1N | 1st-Ig | IgG1 | A-1 | +++ | — | N.D. |
| B1511A | sROBO1-His | 5th-Ig | IgM | A-1 | + | 4.6 | 41.5 |
| B2212A | ROBO1gp4 | 3rd-FnIII | IgG2a | A-1 | + | 4.9 | 36.2 |
| B2318C | ROBO1gp4 | 3rd-FnIII | IgG2a | A-2 | ++ | 101.6 | 27.7 |
| B2542A | ROBO1gp2 | 3rd-Ig | IgG3 | A-1 | + | — | — |
| B2610A | ROBO1gp4 | 3rd-FnIII | IgG1 | A-1 | + | 6.1 | 35.4 |
| B4704A | ROBO1-Full | 5th-Ig | IgG2a | A-1 | + | 140466.7 | 58.8 |
| B5202A | ROBO1-Full | 5th-Ig | IgG2a | A-1 | + | 14.8 | 58.7 |
| B5209B | ROBO1-Full | 5th-Ig | IgG2b | A-1 | ++ | 3.1 | 87.2 |
| B5303A | ROBO1-Full | 5th-Ig | IgG2a | A-1 | ++ | 7.3 | 79.2 |
| B5304A | ROBO1-Full | 1st-FnIII | IgG2b | A-1 | + | 954.7 | 32.8 |
| B5309D | ROBO1-Full | 5th-Ig | IgG2a | A-1 | + | 70.4 | 34.9 |
| B5310C | ROBO1-Full | 5th-Ig | IgG1 | A-1 | + | 10.7 | — |
| B5315C | ROBO1-Full | 5th-Ig | IgG2a | A-1 | + | 22.5 | 51 |
| B5317B | ROBO1-Full | 5th-Ig | IgG2b | A-1 | + | 52.7 | 86.4 |

FACS score: FACA analysis against ROBO1-expressing HEK cell; EC50(nM) obtained by digitizing signal intensity; IgG = 150 kD.
CDC score: measured value (%) at 0.1 ug/mL
N.D.: Not tested
B2212A: It belongs to B2318 series (gb4_BV/gp64TGM + CD40L) due to error in picking up a clone.
B2318C: It belongs to B2212 series (gb4_BV/gp64TGM) due to error in picking up a clone of evaluation of antibody concentration-dependent CDC activities (FIG. 8B). As a result, it became clear that B5209B (IgG2b) had the highest CDC activity.

(3) Epitope analysis of anti-ROBO1 monoclonal antibody

Expression of various types of GST-bound proteins as shown in FIG. 6 was analyzed. In the case of Ig2_GST and Ig5_GST, no proteins were detected in both soluble and insoluble fractions, and thus other types of GST-bound proteins were used in epitope analysis (Ig2_GST and Ig4-5_GST). The results obtained by detection of expression of each domain with an anti-GST antibody are shown in FIG. 10. Except for Ig3_GST, only trace amounts of immunoglobulin domains Ig1, 2-3, 4, and 4-5_GST were detected in soluble fractions. Thus, insoluble fractions were used in epitope analysis. For fibronectin III domains Fn1, 2, 3_GST, and UT1_GST, soluble fractions were used.

First, B2318C, B2212A and B2610A, which were antibodies obtained by immunization with gp4_BV, were subjected to epitope analysis. As shown in FIG. 6, since an antigen portion comprises a site ranging from upstream of a transmembrane region to the third fibronectin III domain (738-855 amino acids), epitope analysis was carried out by the Western blot method using Fn3_GST and UT1_GST. As a result, as shown in FIG. 11A, all sites did not bind to UT1_GST, but bound to Fn3. Thus, it became clear that each recognition site was the third fibronectin III domain.

(C) Consideration

As a result of characterization of anti-ROBO1 monoclonal antibodies obtained in the present studies, the CDC activity of each antibody, the binding ability of each antibody to ROBO1 on the cell surface (FACS analysis), and a ROBO1-binding domain (epitope) were revealed. Among the three types of immunization methods conducted in the present studies, a method of immunizing gp64TGM with ROBO1-Full_BV was most successful in isolation of an antibody having cytotoxicity. Also, it is noteworthy that the used serum was changed from FCS (fetal calf serum) to CS (calf serum).

It was only the third fibronectin domain (gp4_BV) that succeeded in obtaining a FACS positive antibody during immunization of each ROBO1 domain with a gp64-bound antigen. In addition, with regard to GST-bound proteins used in epitope mapping, fibronectin domains easily became soluble in an *Escherichia coli* expression system. In the case of immunoglobulin domains other than the third domain, the second and fifth domains were not expressed, and the first and fourth domains were insoluble. Taking into consideration such circumstances, it was suggested that partial expression was not preferable in production of an antibody reacting with a region wherein cysteine or the like has a great influence on a steric structure, such as an immunoglobulin domain.

Moreover, the epitopes of antibodies having cytotoxicity obtained by immunization with antigens comprising the entire ROBO1 extracellular region, ROBO1-Full_BV and sROBO1-His, were all the fifth immunoglobulins except for 1 case (Table 3). Since FACS negative clones were not selected in a screening process, it is considered that in reality, there was a possibility that FACS negative antibodies that recognized other epitopes were produced in a mouse spleen. With regard to other sites (domains), there was a possibility that the steric structure of an immunogen was not similar to the steric structure of the cell surface. There was also a possibility that an antibody reacting with the fifth immunoglobulin was easily produced for some reason.

Using the produced antibody panel (Table 3), optimal epitope sites were analyzed. Three points, namely, the isotype of an antibody, the affinity of an antibody for ROBO1, and an antigen-binding site were considered to have an influence on the level of CDC activity or the like. Thus, by comparing two antibodies having the same isotype and the same level of affinity, an optimal antigen-binding site could be assumed. The isolated B2212A and B5303A were both IgG2a, and the affinity (EC50 value) in the FACS analysis was 7.3 nM and 4.9 nM, which were close values (FIG. 12A). The fact that the cytotoxicity of B5303A was clearly higher than that of B2212A (FIG. 12B) suggested that when the fifth fibronectin domain would be targeted, cytotoxicity would be easily induced, rather than when the third fibronectin domain would be targeted.

Example 3

Extracorporeal Imaging of Tumor by PET (A) Method (1) $^{18}$FDG Study

Animal used: $10^7$ HepG2 cells were transplanted into a 6-week-old BALB/cAjc1-nu/nu male mouse, so as to produce a xenograft model. When this model was subjected to an experiment, it was 9 week old, having a tumor size of 10×8 nm and a body weight of 25 g.

Anesthesia: Isoflurane inhalation anesthesia was performed on the model, using a handmade inhalation anesthesia apparatus for small animals. The state of spontaneous respiration was monitored with a videocamera, and a breathing rate and an anesthetic concentration were recorded at regular intervals.

Heat retention: In order to avoid a decrease in the body temperature, the model animal was prevented from directly coming into contact with the outside air using a handmade transparent cover. A small amount of halogen lamp light was indirectly applied from outside of the scanner for heat retention. The temperature in the room and that in the cover were recorded at regular intervals. Radiopharmaceutical used and administration method thereof: Approximately 0.8 mCi (10 MBq) of $^{18}$FDG ($^{18}$F half-life: 110 minutes) was administered via an intravenous line over approximately 1 minute using a handmade cannulation apparatus produced from a 27G needle.

Photographic device and PET data collection protocol: MicroPET Focus 120 manufactured by Siemens (FIG. 1, lower right) was used to collect dynamic image data at 20 sec×6, 60 sec×6, 2 min×6, and 5 min×8 (26 frames in total; 60 minutes).

(2) $^{64}$Cu-DOTA-anti-Robo1 whole IgG mAb study

Animal used: The two above HepG2 cell xenograft models were used when they were 17 weeks old. The two model animals were subjected to fasting from the night before the first day of experiment until termination of the experiment on the first day. The tumor size of Mouse# 1 and that of Mouse#2 were 15 mm×13 mm and 18 mm×12 mm, respectively. For 5 days of the experiment (Jan. 16-20, 2007), the body weight of Mouse#1 and that of Mouse#2 were 22-26 g and 19-21 g, respectively. After completion of the experiment on the last day (Jan. 20, 2007), a tumor portion was excised, and it was then fixed with formalin. Portions other than the tumor portion were frozen for preservation.

Synthesis of radiopharmaceutical: Positron nuclide $^{64}$Cu (half-life: 12.7 hours) was produced via a $^{64}$Ni(pn)$^{64}$Cu reaction at S. H. I. E. Examination & Inspection, Ltd. (Niihama-shi, Ehime). Subsequently, at the First Radioisotope (Matsuo-cho, Chiba), a bifunctional chelating agent 1,4,7,10-tetraazacyclododecane-1,4,7,10-tetraacetic acid (DOTA) was introduced into anti-Robo1 mAb (the monoclonal antibody B5209B produced in Example 1) via a highly reactive isothiocyanate group. Finally, DOTA mAb was labeled with $^{64}$Cu, and the activity was then evaluated.

Specification of radiopharmaceutical: The radioactive concentration of the $^{64}$Cu-DOTA-anti-Robo1 whole IgG monoclonal antibody was 23.3 MBq/ml (in 511 KeV measurement, however, it was 16.4 MBq/ml). The amount of liquid administered was 0.8 ml (Mouse#1) and 0.5 ml (Mouse#2). When administered, it became approximately 9 MBq and 6 MBq (511 Kev window), respectively. The antibody concentration was 0.331 mg/ml.

Anesthesia and heat retention: The anesthetic method and the heat retention method were the same as those in the FDG study. In order to collect MicroPET data, each mouse was subjected to several times of anesthesia PET data collection protocol: 0.8 ml of $^{64}$Cu-DOTA mAb solution was administered to Mouse#1 via an indwelling venous line over 5 minutes. In addition, 0.5 ml of the solution was administered to Mouse#2. Data collection was carried out from immediately after the administration to the $4^{th}$ day, for 22.5 hours 8 times in total in the case of Mouse#1, and for 18.5 hours 6 times in total in the case of Mouse#2. The final scanning (data collection time: 8 hours) was carried out 4 days after the administration, namely, after the nude mouse had been subjected to euthanasia.

Image reconstruction and image data analysis (outline): The collected PET data, both Part 1 and Part 2, were subjected to a series of treatments. Finally, the data were reconstructed to 3D or 4D image by the Filtered Back Projection method (in the case of dynamic data collection). Image display was set at a region of interest (ROI), and a time activity curve (TAC) was calculated using MicroPET software, AsiPro.

(B) Results (1) $^{18}$FDG Study

The image obtained 55-60 minutes after administration of $^{18}$FDG to the HepG2 tumor nude mouse is shown in FIG. 13. It was confirmed that the level of $^{18}$FDG accumulated in a HepG2 tumor portion is lower than the level of $^{18}$FDG accumulated in a heart or a brain having high hexokinase activity, and that the level of $^{18}$FDG accumulated in a HepG2 tumor portion is higher than that in a liver in which a $^{18}$FDG metabolite is decomposed due to dephosphorylation.

Total 26 frames of dynamic images taken in the same coronal section from immediately after administration of $^{18}$FDG until 60 minutes have passed are shown in FIG. 14. The bloodstream of renal artery in the bloodstream phase immediately after the administration (FIG. 14A), a tumor image at an initial stage (FIG. 14B), a urinary bladder imaged with RI egested into urine (FIG. 14C), accumulation of tumor considered to be due to the metabolic trapping of $^{18}$FDG (FIG. 14D), accumulation of the agent in a liver (FIG. 14E), and accumulation of the agent in a cardiac muscle (FIG. 14F) were shown as RI dynamic images of the whole mouse body, without moving the bed to extend a scanning range.

A time activity curve (TAC) was obtained from three regions of interest (ROI) that had been set to easily evaluate the drug disposition of $^{18}$FDG in each organ, namely, a liver, a kidney, and a HepG2 tumor portion (FIG. 15). For 60 minutes after administration of $^{18}$FDG, accumulation of the agent in the kidney was always highest. Accumulation of the agent in the HepG2 tumor was gradually increased, and approximately 12 minutes later, accumulation of the agent in the HepG2 tumor became higher than that in a normal liver.

Supplement: Additional $^{18}$FDG Study with lung cancer xenograft

The $^{18}$FDG image in a lung squamous cell carcinoma QG-56 nude mouse that was taken 60 minutes later is shown in FIG. 16. On the PET image, a low level of the agent was accumulated in the lung squamous cell carcinoma xenograft, or no agents were accumulated therein. With regard to a tumor tissue cleavage plane, no solid tumor components were observed in the tumor.

(2) $^{64}$Cu-DOTA-anti-Robo 1 whole IgG mAb Study

PET images taken 6 hours, 1 day, 2 days, and 3 days after administration of $^{64}$Cu-DOTA-anti-Robo1 whole IgG mAb to Mouse#1 are shown in FIG. 17. In the 6-hour image, accumulation of the agent in the HepG2 tumor was lower than the blood pool image in a cardiac lumen. However, accumulation of the agent in the tumor was gradually increased until 3 days after the administration. $^{64}$Cu-DOTA mAb non-specifically accumulated in the liver was slowly egested to an intestinal canal via a biliary system. No accumulation of the agent in a kidney and a urinary bladder were confirmed.

PET images taken 1 day, 2 days, and 3 days after administration of $^{64}$Cu-DOTA-anti-Robo1 whole IgG mAb to Mouse#2 are shown in FIG. 18. 1 day later, accumulation of the agent in the tumor was lower than accumulation of the agent in the normal liver, and distribution of $^{64}$Cu-DOTA-anti-Robo1 mAb could not confirmed in several portions of the tumor. Three days later, however, it was confirmed that the agent was distributed to the entire tumor volume at a high accumulation level.

Distribution of $^{64}$Cu-DOTA-anti-Robo1 mAb (including a $^{64}$Cu-labeled decomposed product) in the body, when the two nude mice were subjected to euthanasia (Mouse #1: 87 hours later; and Mouse #2: 84 hours later), is shown in FIG. 19. Accumulation of the agent in the HepG2 tumor was highest among the organs of the entire body. It is reasonable to understand that accumulation of the agent in the HepG2 tumor is caused by the specific binding of a labeled antibody to a Robo1 antigen. Low levels of accumulations observed outside of the Mouse #1 tumor accorded well with necrosis (approximately 30% of the entire tumor volume) that was macroscopically confirmed after completion of the PET experiment.

BRIEF DESCRIPTION OF THE DRAWINGS

FIG. 1 shows the design of an antigen used to produce an anti-monoclonal antibody.

FIG. 2 shows ROBO1 cloned from Alexander cells and ROBO1 deposited with GenBank under No. NM133631.

FIG. 3 shows the results obtained by confirming expression of various types of BV antigen by the Western blot method. A and B show detection of a gp64 antigen with an anti-gp64: antibody (1:10000). C shows detection of ROBO1-Full_BV with an anti-V5 antibody (1:50000).

FIG. 7 shows the FACS analysis of ROBO1-expressing HEK293 cells using an anti-ROBO1 monoclonal antibody. In A and C, fluorescence intensities were converted to numbers, and they were compared using line graphs. In B, fluorescence intensities were compared using bar graphs.

FIG. 8 shows a test to examine the CDC activity of an anti-ROBO1 monoclonal antibody on ROBO1-expressing HEK293 cells. A shows the CDC activity of the antibody obtained by immunization with a gp64-BV antigen. B shows the comparison made between the CDC activity of the antibody obtained by immunization with ROBO1-Full_BV and that of B2318C.

FIG. 10 shows a GST-binding protein used in the epitope analysis of an anti-ROBO1 monoclonal antibody. The symbol Ig indicates an immunoglobulin domain and Fn indicates a fibronectin III domain. As an Ig sample, an insoluble fraction is used in all cases. As Fn, UT1, and GST_Control, a soluble fraction is used.

FIG. 12 shows the comparison between B2212A (IgG2a, epitope 3rd-FnIII) and B5303A (IgG2a, epitope 5th-Ig). A shows the comparison between the results obtained by the FACS analysis of B2212A to ROBO1-expressing HEK293 cells and the results obtained by the FACS analysis of B5303A to ROBO1-expressing HEK293 cells. B shows the comparison between the CDC activity of B2212A on ROBO1-expressing HEK293 cells and the activity of CDC activity of B5303A on ROBO1-expressing HEK293 cells.

SEQUENCE LISTING

<160> NUMBER OF SEQ ID NOS: 36

Figure 4:
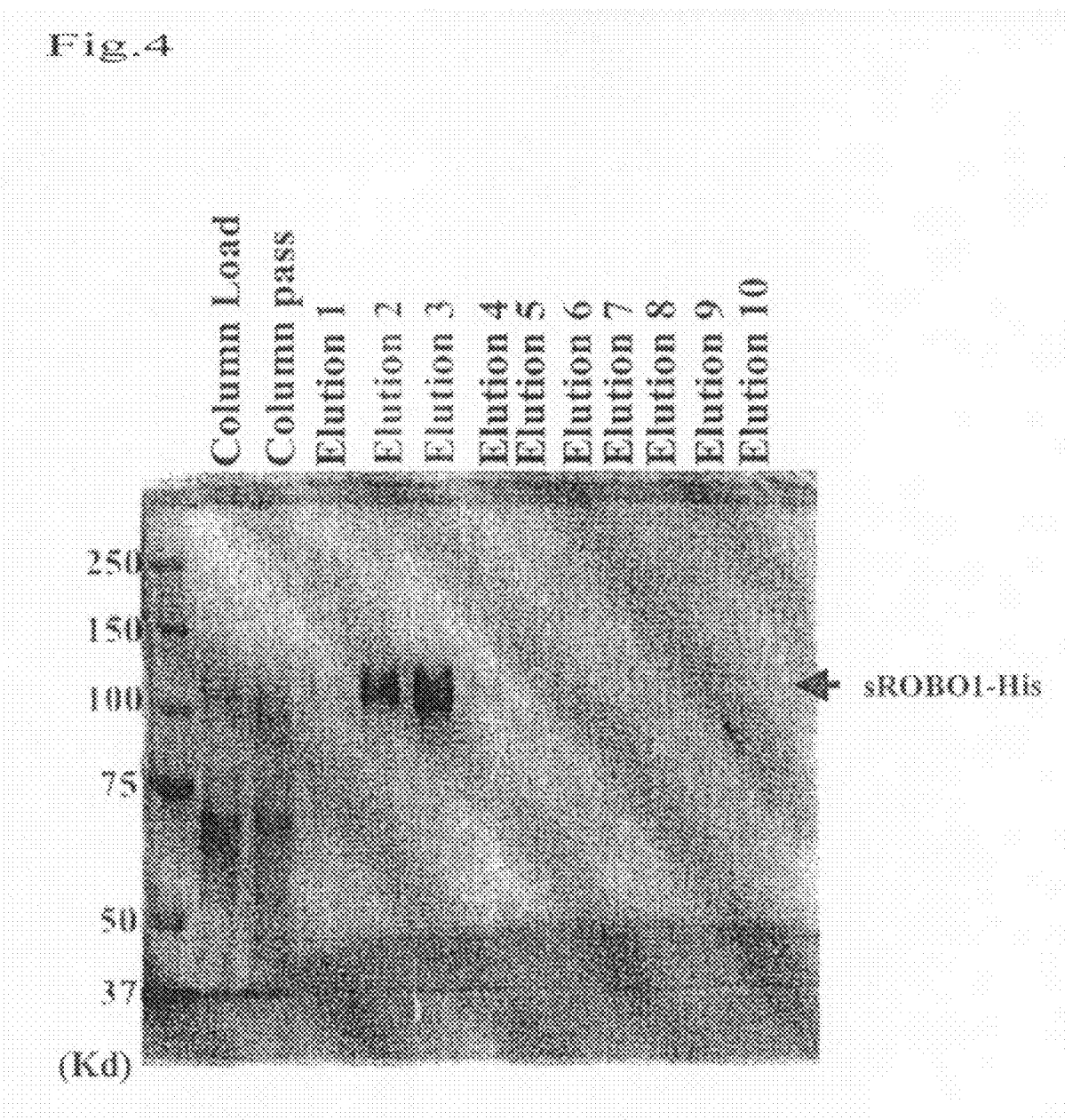
FIG. 4 shows affinity purification of sROBO1-His with a Ni-NTA column. For each case, the following conditions are applied: application of 10 µl, CBB staining, and the use of 10%_Gel.
Figure 5A:
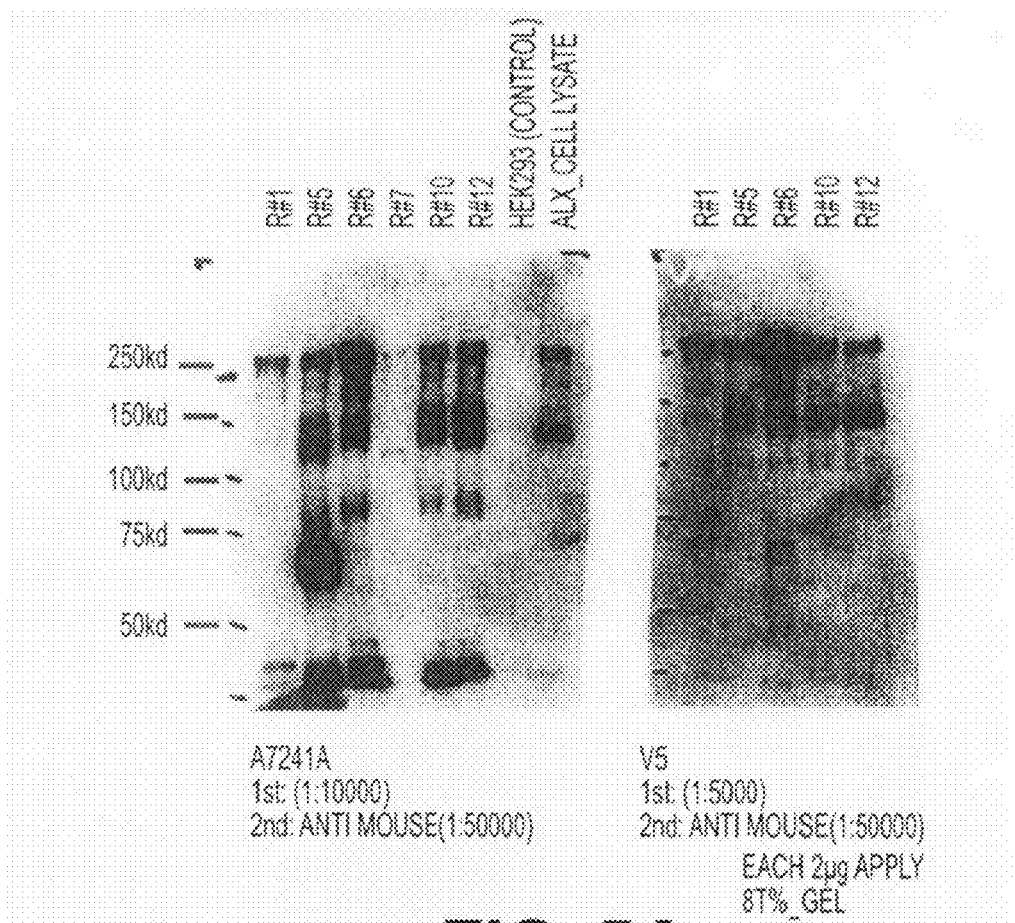
FIG. 5 shows the screening of ROBO1-expressing HEK293 cells. A shows the analysis of a cell lysate by the Western blot method. B shows the FACS analysis of ROBO1-expressing HEK293 cells.
Figure 5B:
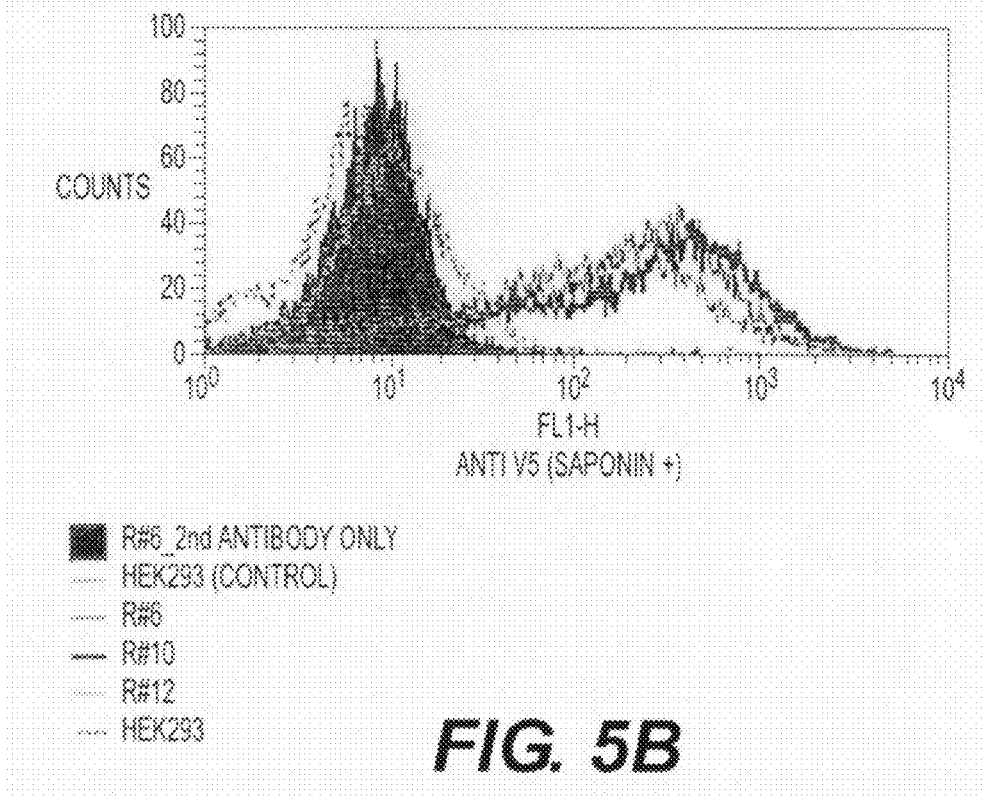
Figure 6:
FIG. 6 shows a GST-binding protein used in the epitope analysis of an anti-ROBO1 monoclonal antibody.
Figure 9A:
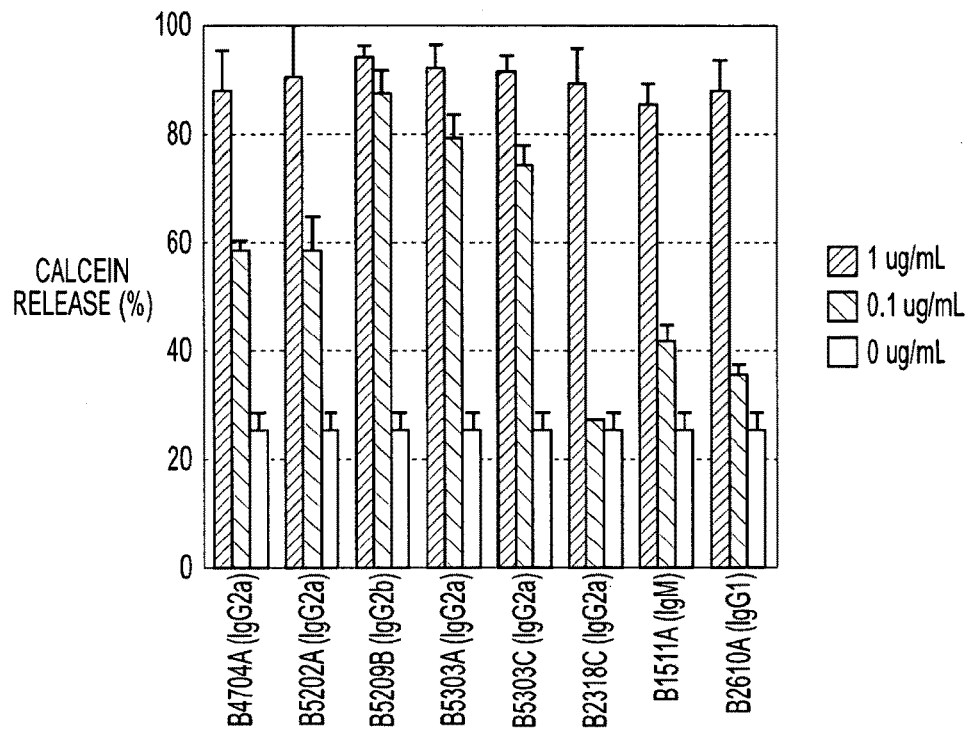
FIG. 9 shows the comparison of the CDC activities of anti-ROBO1 monoclonal antibodies. A and B show the comparison of the CDC activities on calcein-labeled ROBO1-expressing HEK293 cells at 5% BRC.
Figure 9B:
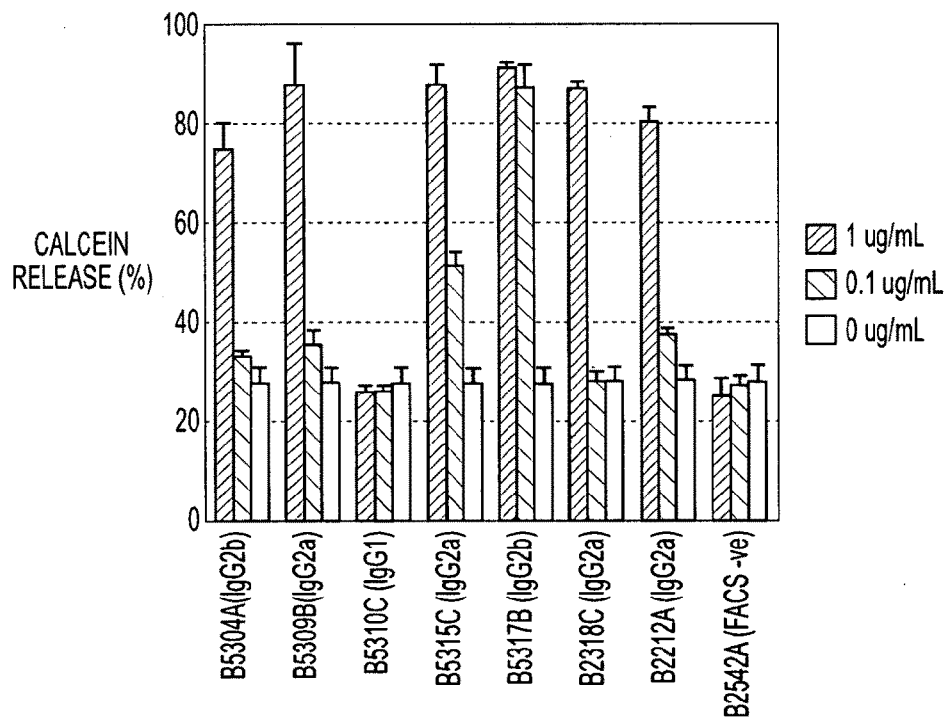
Figure 11:
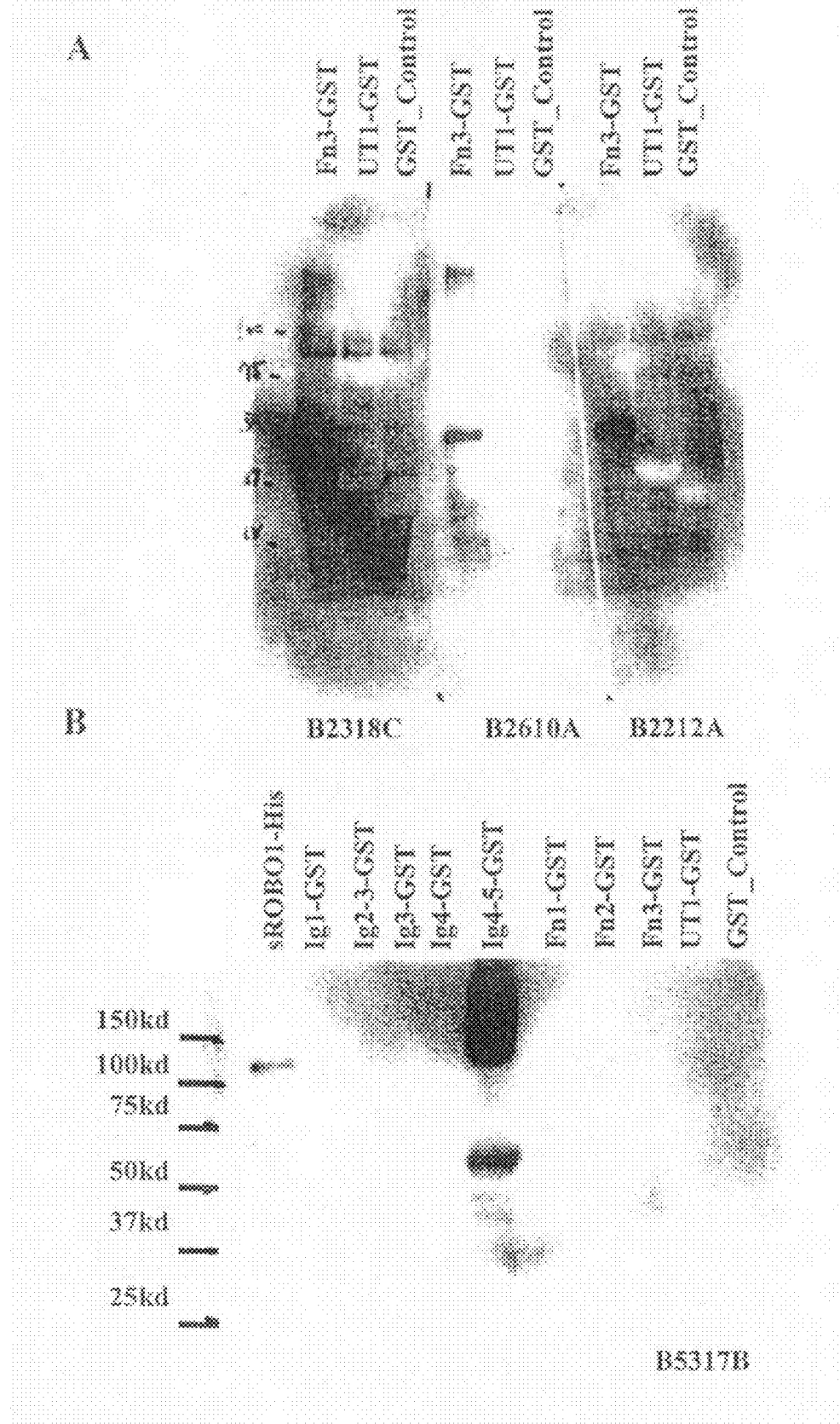
FIG. 11 shows the epitope mapping of an anti-ROBO1 monoclonal antibody. A shows the epitope mapping of an antibody obtained by immunization with gp4BV (Fniii-3$^{rd}$) that was a gp64-bound antigen. B shows the epitope mapping of B5317B obtained by immunization with ROBO1-Full_BV
Figure 13:
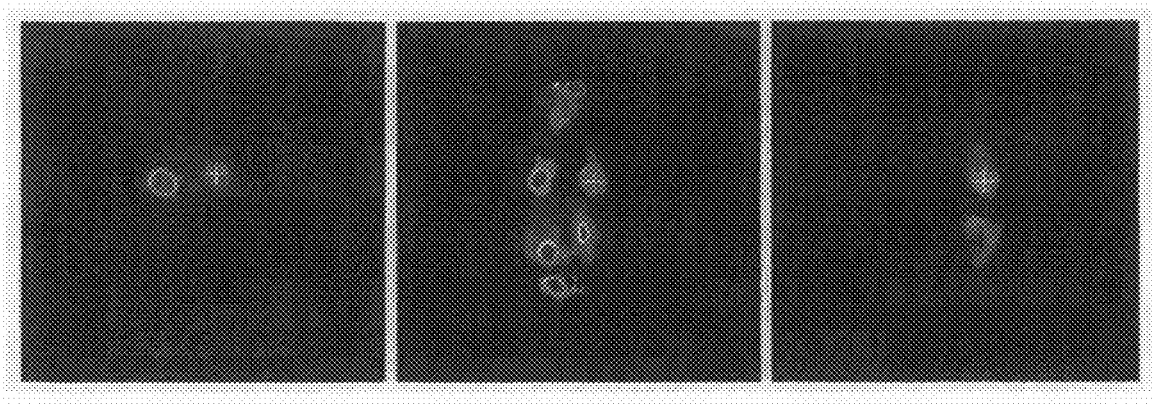
FIG. 13 shows the imaging of a HepG2 tumor nude mouse for 55 to 60 minutes after administration of $^{18}$FDG There are three-way cross-sectional images crossing over a tumor portion indicated with a yellow cross (axial, coronal, and sagittal cross-sectional images from the left side). Accumulation of arrows indicates a tumor. In the coronal image at the center, favorable accumulation of the agent in a cardiac muscle and a brain, in which active sugar metabolism kexokinase) occurs, is confirmed. Further, a nephros as an excretory pathway and RI retention in a urinary bladder are imaged.
Figure 14:
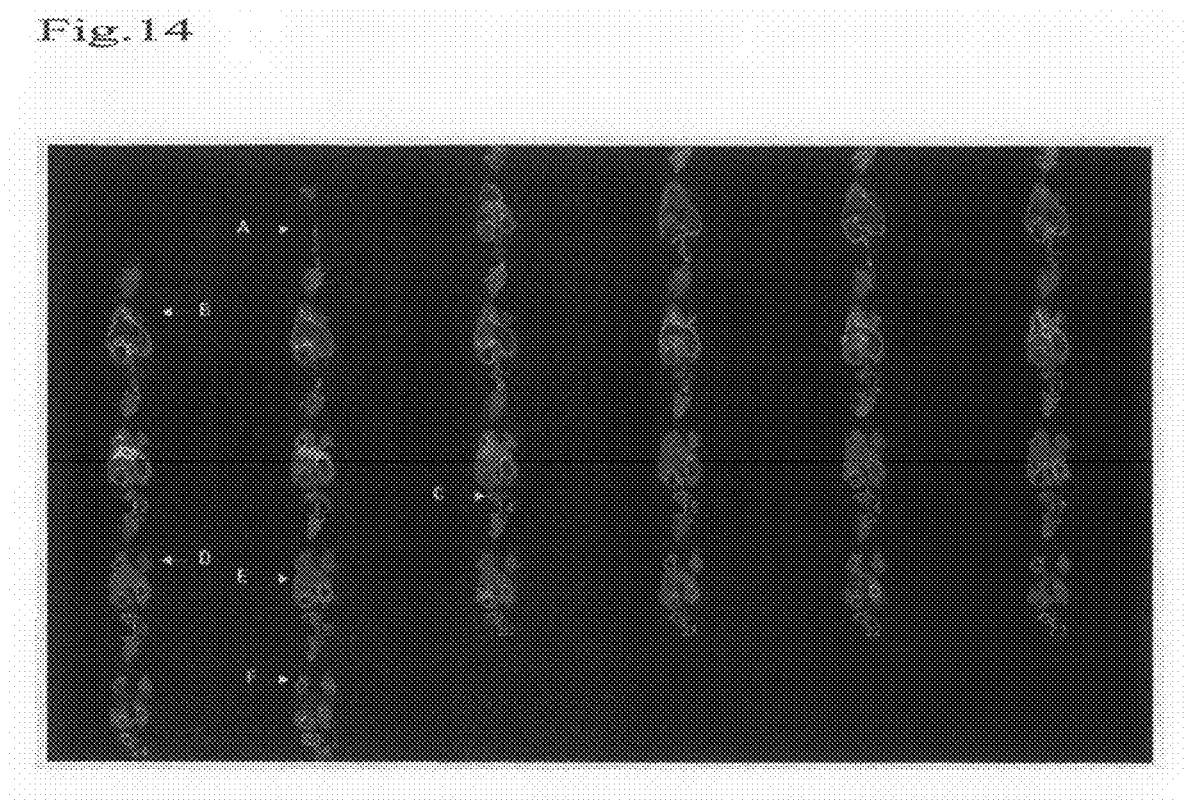
FIG. 14 shows an image obtained during a period from immediately after administration of $^{18}$FDG until 60 minutes have passed (which indicates a single cross section; 26 frames; and 20 sec×6, 60 sec×6, 2 min×6, and 5 min×8). The upper left indicates a bloodstream (artery) phase obtained immediately after administration of RI, and the lower right indicates such a bloodstream obtained 60 minutes after the administration. A indicates the bloodstream of renal artery, B indicates a tumor image at an initial stage, C indicates a urinary bladder imaged with RI egested into urine, D indicates a tumor image, E indicates accumulation of the agent in a liver, and F indicates accumulation of the agent in a cardiac muscle.
Figure 15:
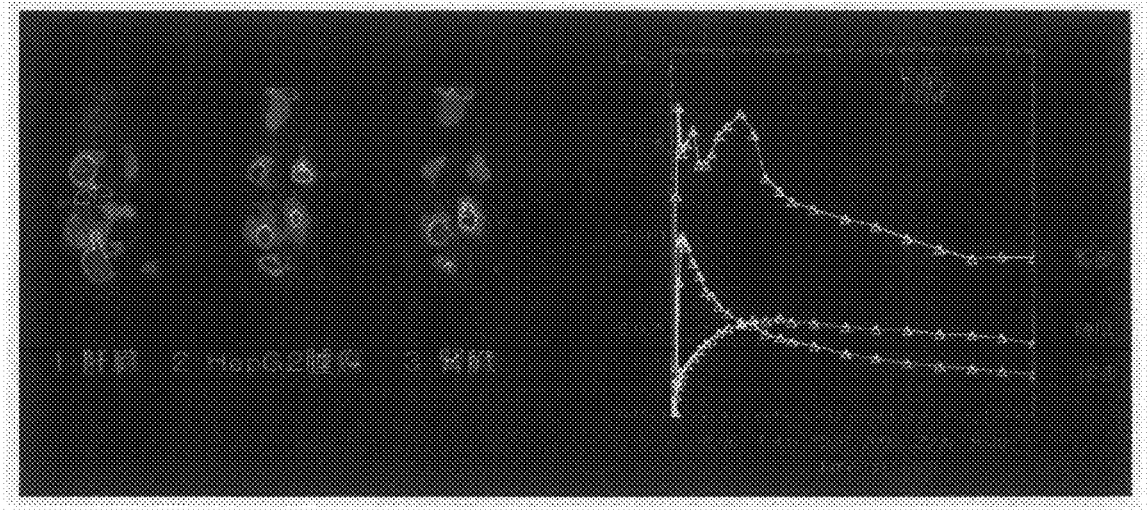
FIG. 15 shows an example of setting regions of interest on the PET image (left) comprising three different reconstruction cross-sections (coronal), and a time activity curve (right) obtained for 60 minutes from the time of administration of $^{18}$FDG obtained from three regions of interest (ROI). The red arrows in the PET image (left) successively indicate the ROI of a liver, the ROI of a HepG2 tumor portion, and the ROI of a kidney, from the left. The x-axis of the time activity curve (TAC, right) indicates time (second), and y-axis indicates of the count rate of PET.
Figure 16:
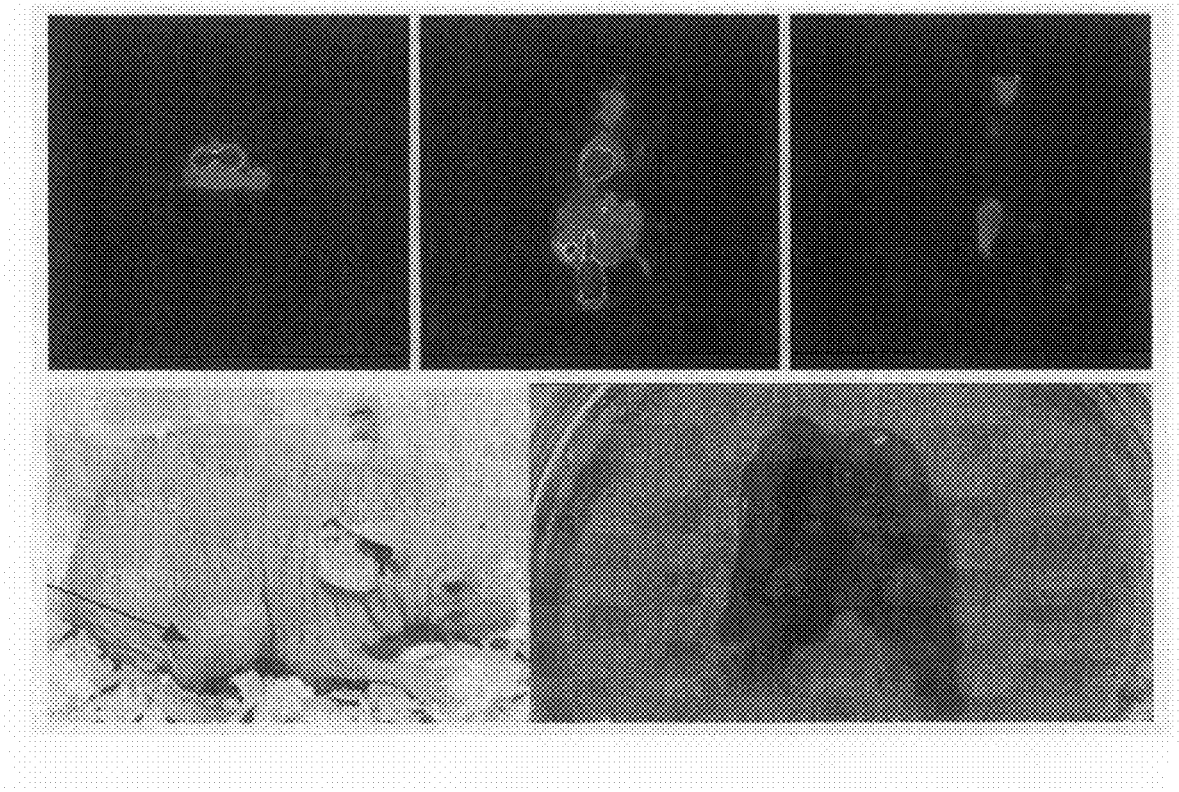
FIG. 16 shows $^{18}$FDG MicroPET Supplementary Images (lung squamous cell carcinoma QG-56 nude mouse, the image obtained after 60 minutes). The red arrows as shown in the PET image (upper stage) and the photograph of the nude mouse (lower left stage) indicate lung squamous cell carcinoma xenografts. Looking at the $^{18}$FDG PET image, the agent was accumulated in the tumor at a low level or was not accumulated at all (upper stage), and in the tumor tissue cleavage plane, no solid tumor components were observed in the tumor (lower right stage).
Figure 17:
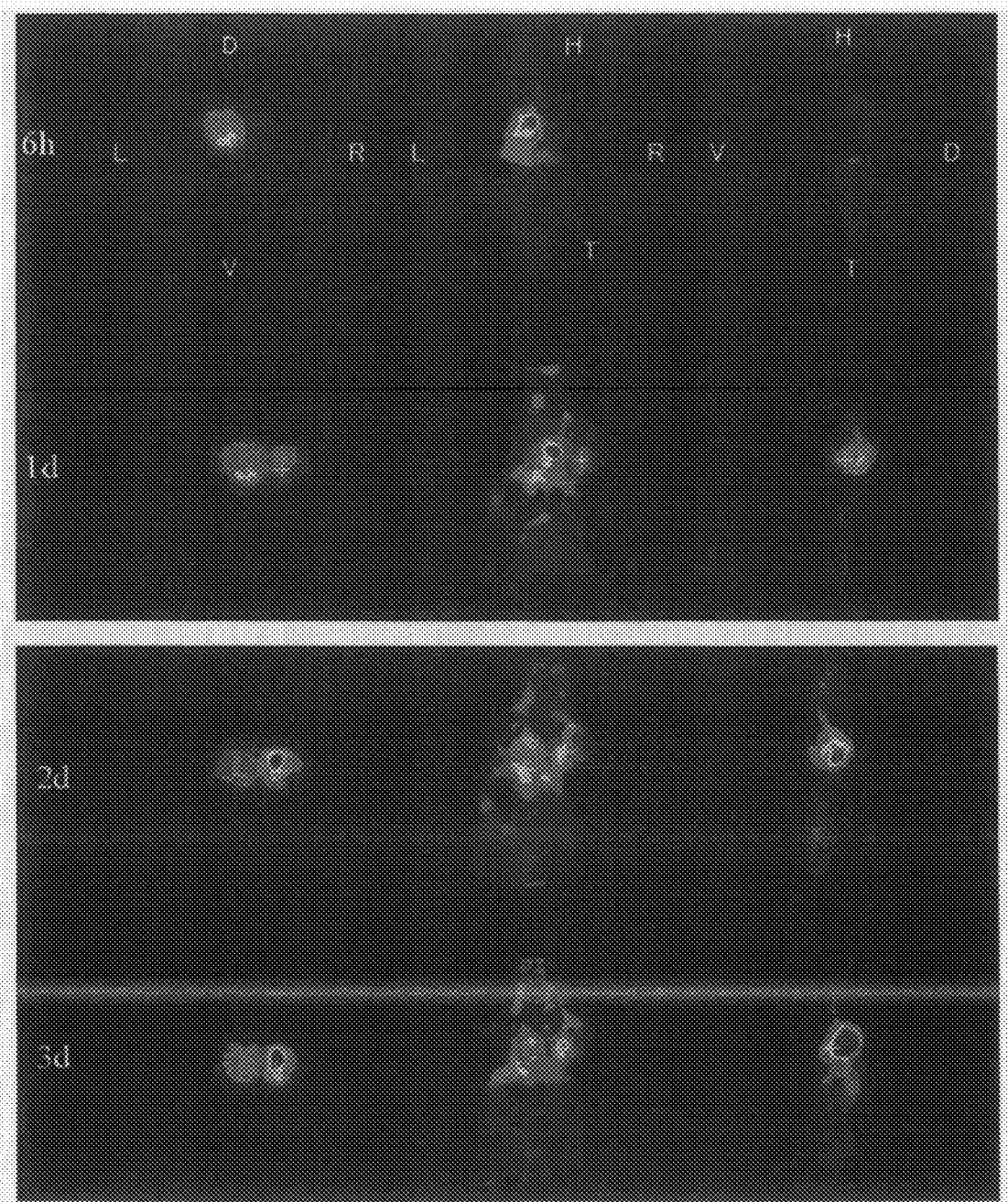
FIG. 17 shows MicroPET images obtained 6 hours, 1 day, 2 days and 3 days after administration of $^{64}$Cu-DOTA-anti-Robo1 whole IgG mAb, from the upper stage (in each of the aforementioned times, axial, coronal, sagital cross-section views are shown from the left, and the maximum accumulation in each time is indicated with a red of the Rainbow color scale, so that the results can be relatively shown). Accumulation of the agent in the tumor observed from the image 6 hours after the administration was smaller than that of a cardiac lumen blood pool image. However, accumulation of the agent in the tumor was relatively increased. Accumulation of the agent in a liver was rather decreased, and it was egested to an intestinal canal. No images of a kidney and a urinary bladder were obtained. (D: doral, V: ventral, L: left, R: right, H: head, and T: tail).
Figure 18:
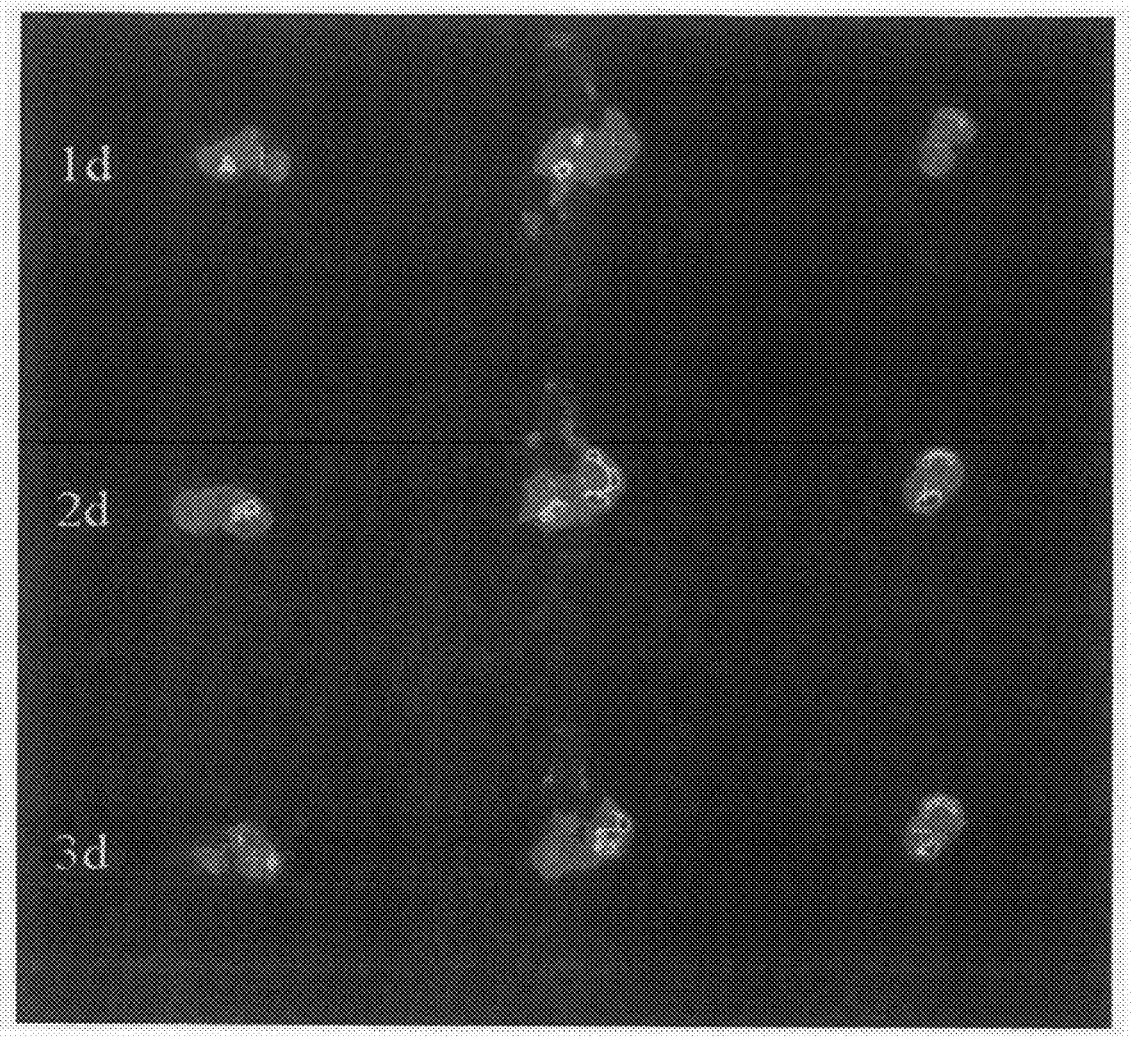
FIG. 18 is a PET image showing a change over time in the accumulation of $^{64}$Cu-DOTA-anti-Robo1 mAb in Mouse #2 (upper stage: 1 day after, middle stage: 2 days after, lower stage: 3 days after the administration; and the yellow cross indicates tumor). 1 day after the administration, the accumulation level of the aforementioned agent into the tumor was lower than the accumulation level of the aforementioned agent into a normal liver. However, 3 days after the administration, accumulation of the agent in the tumor reached the highest level. From the image obtained 1 day after the administration, distribution of $^{64}$Cu-DOTA-anti-Robo1 mAb into the tumor was not clearly observed, but 8 days later, distribution of the aforementioned agent into the entire tumor volume was observed.
Figure 19:
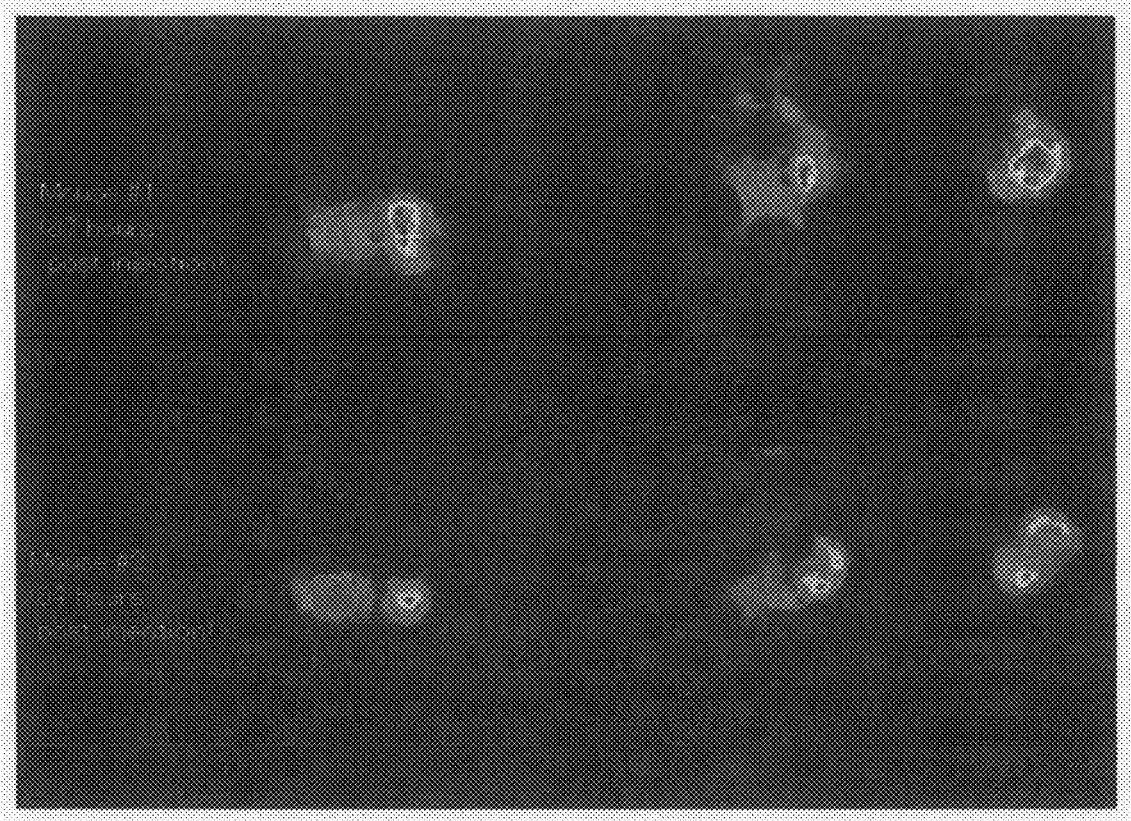
FIG. 19 shows distribution of $^{64}$Cu-DOTA-anti-Robo1 mAb (including a $^{64}$Cu-labeled decomposed product) in the body of each mouse, when the nude mice were subjected to euthanasia (upper stage: Mouse #1, 87 hours later; and lower stages: Mouse #2, 84 hours later). It is reasonable to understand that accumulation of the agent in the HepG2 tumor is caused by the specific binding of a labeled antibody to a Robo1 antigen. Low levels of accumulations observed outside of the Mouse #1 tumor (upper left stage and center) are considered to be necrosis.

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
accatgattg cggagcccgc tcac                                            24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctttcagtt tcctctaatt c                                               21

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ggtacccctt cgtcaggaag attttccac                                   29

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtaccgagt aattccttgc tacaca                                      26

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtacccgat gaaggagtct atgtctgtgt                                  30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtaccgcac caacacaaac atatttgcca                                  30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtacccacc aatatggttg gggaacgtga                                  30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtaccgcag atgcttcagc tttgcccacc                                  30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtacccgct aatgcatatg gaattagtga                                          30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtaccgcat tcttggatac agttacacct                                          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtacccgca cccagtgccc caccccaagg                                          30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtaccgcat ctgaaatctg ctgagcgagg                                          30

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accatgattg cggagcccgc tcac                                                24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggccggctgc ttcaccacat                                                     20

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
ggatccgatg attgcggagc ccgctcactt ttacc                                35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagcttgaca tccgaagggt tttgtctgaa gtcat                                35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggatccgaat gcatcgctgg aagtagccat acttc                                35

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagcttactg ggtctcttca caaatgatgg tctc                                 34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggatccggag agtgaagtag ccgagctgac tgtc                                 34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aagcttccgt cccaaagcaa caacctggtc acgg                                 34

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```

```
ggatccgccc cgtgaccagg ttgttgcttt g                                      31
```

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
aagctttaca gtctgattca caggaccttg tcg                                    33
```

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
ggatccgatc atcacaaagg catatttgga ag                                     32
```

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
aagctttgta tttctgctga catctgtcac ttc                                    33
```

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
ggatccgcca aatttaatcc ctagtgcccc atc                                    33
```

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
aagcttaagg acggtggggt tgtggaggtg cag                                    33
```

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggatccgaag caggtccaga gagagctggg aaatg                                35

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagcttcttg gatacagtta caccttgggg tgg                                  33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggatccgttt gccaaaaccc tggaagaagc acc                                  33

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agcttctgct tcaccacatc tgaaatctgc tg                                   32

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggatccgcag ttcatccagc tggatgcc                                        28

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagcttctgc ttcaccacat ctgaaatctg ctg                                  33

<210> SEQ ID NO 33
<211> LENGTH: 960
<212> TYPE: PRT
<213> ORGANISM: Homo sapiens

<400> SEQUENCE: 33

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val

-continued

```
                     20                  25                  30
Glu His Pro Ser Asp Leu Ile Val Ser Lys Gly Glu Pro Ala Thr Leu
        35                  40                  45
Asn Cys Lys Ala Glu Gly Arg Pro Thr Pro Thr Ile Glu Trp Tyr Lys
 50                  55                  60
Gly Gly Glu Arg Val Glu Thr Asp Lys Asp Pro Arg Ser His Arg
65                  70                  75                  80
Met Leu Leu Pro Ser Gly Ser Leu Phe Phe Leu Arg Ile Val His Gly
                85                  90                  95
Arg Lys Ser Arg Pro Asp Glu Gly Val Tyr Val Cys Val Ala Arg Asn
            100                 105                 110
Tyr Leu Gly Glu Ala Val Ser His Asn Ala Ser Leu Glu Val Ala Ile
        115                 120                 125
Leu Arg Asp Asp Phe Arg Gln Asn Pro Ser Asp Val Met Val Ala Val
    130                 135                 140
Gly Glu Pro Ala Val Met Glu Cys Gln Pro Pro Arg Gly His Pro Glu
145                 150                 155                 160
Pro Thr Ile Ser Trp Lys Lys Asp Gly Ser Pro Leu Asp Asp Lys Asp
                165                 170                 175
Glu Arg Ile Thr Ile Arg Gly Gly Lys Leu Met Ile Thr Tyr Thr Arg
            180                 185                 190
Lys Ser Asp Ala Gly Lys Tyr Val Cys Val Gly Thr Asn Met Val Gly
        195                 200                 205
Glu Arg Glu Ser Glu Val Ala Glu Leu Thr Val Leu Glu Arg Pro Ser
    210                 215                 220
Phe Val Lys Arg Pro Ser Asn Leu Ala Val Thr Val Asp Asp Ser Ala
225                 230                 235                 240
Glu Phe Lys Cys Glu Ala Arg Gly Asp Pro Val Pro Thr Val Arg Trp
                245                 250                 255
Arg Lys Asp Asp Gly Glu Leu Pro Lys Ser Arg Tyr Glu Ile Arg Asp
            260                 265                 270
Asp His Thr Leu Lys Ile Arg Lys Val Thr Ala Gly Asp Met Gly Ser
        275                 280                 285
Tyr Thr Cys Val Ala Glu Asn Met Val Gly Lys Ala Glu Ala Ser Ala
    290                 295                 300
Thr Leu Thr Val Gln Val Gly Ser Glu Pro Pro His Phe Val Val Lys
305                 310                 315                 320
Pro Arg Asp Gln Val Val Ala Leu Gly Arg Thr Val Thr Phe Gln Cys
                325                 330                 335
Glu Ala Thr Gly Asn Pro Gln Pro Ala Ile Phe Trp Arg Arg Glu Gly
            340                 345                 350
Ser Gln Asn Leu Leu Phe Ser Tyr Gln Pro Pro Gln Ser Ser Ser Arg
        355                 360                 365
Phe Ser Val Ser Gln Thr Gly Asp Leu Thr Ile Thr Asn Val Gln Arg
    370                 375                 380
Ser Asp Val Gly Tyr Tyr Ile Cys Gln Thr Leu Asn Val Ala Gly Ser
385                 390                 395                 400
Ile Ile Thr Lys Ala Tyr Leu Glu Val Thr Asp Val Ile Ala Asp Arg
                405                 410                 415
Pro Pro Pro Val Ile Arg Gln Gly Pro Val Asn Gln Thr Val Ala Val
            420                 425                 430
Asp Gly Thr Phe Val Leu Ser Cys Val Ala Thr Gly Ser Pro Val Pro
        435                 440                 445
```

```
Thr Ile Leu Trp Arg Lys Asp Gly Val Leu Val Ser Thr Gln Asp Ser
    450                 455                 460

Arg Ile Lys Gln Leu Glu Asn Gly Val Leu Gln Ile Arg Tyr Ala Lys
465                 470                 475                 480

Leu Gly Asp Thr Gly Arg Tyr Thr Cys Ile Ala Ser Thr Pro Ser Gly
                    485                 490                 495

Glu Ala Thr Trp Ser Ala Tyr Ile Glu Val Gln Glu Phe Gly Val Pro
                500                 505                 510

Val Gln Pro Pro Arg Pro Thr Asp Pro Asn Leu Ile Pro Ser Ala Pro
            515                 520                 525

Ser Lys Pro Glu Val Thr Asp Val Ser Arg Asn Thr Val Thr Leu Ser
530                 535                 540

Trp Gln Pro Asn Leu Asn Ser Gly Ala Thr Pro Thr Ser Tyr Ile Ile
545                 550                 555                 560

Glu Ala Phe Ser His Ala Ser Gly Ser Ser Trp Gln Thr Val Ala Glu
                565                 570                 575

Asn Val Lys Thr Glu Thr Ser Ala Ile Lys Gly Leu Lys Pro Asn Ala
                580                 585                 590

Ile Tyr Leu Phe Leu Val Arg Ala Ala Asn Ala Tyr Gly Ile Ser Asp
            595                 600                 605

Pro Ser Gln Ile Ser Asp Pro Val Lys Thr Gln Asp Val Leu Pro Thr
            610                 615                 620

Ser Gln Gly Val Asp His Lys Gln Val Gln Arg Glu Leu Gly Asn Ala
625                 630                 635                 640

Val Leu His Leu His Asn Pro Thr Val Leu Ser Ser Ser Ile Glu
                645                 650                 655

Val His Trp Thr Val Asp Gln Gln Ser Gln Tyr Ile Gln Gly Tyr Lys
            660                 665                 670

Ile Leu Tyr Arg Pro Ser Gly Ala Asn His Gly Glu Ser Asp Trp Leu
            675                 680                 685

Val Phe Glu Val Arg Thr Pro Ala Lys Asn Ser Val Val Ile Pro Asp
690                 695                 700

Leu Arg Lys Gly Val Asn Tyr Glu Ile Lys Ala Arg Pro Phe Phe Asn
705                 710                 715                 720

Glu Phe Gln Gly Ala Asp Ser Glu Ile Lys Phe Ala Lys Thr Leu Glu
                725                 730                 735

Glu Ala Pro Ser Ala Pro Pro Gln Gly Val Thr Val Ser Lys Asn Asp
                740                 745                 750

Gly Asn Gly Thr Ala Ile Leu Val Ser Trp Gln Pro Pro Glu Asp
            755                 760                 765

Thr Gln Asn Gly Met Val Gln Glu Tyr Lys Val Trp Cys Leu Gly Asn
            770                 775                 780

Glu Thr Arg Tyr His Ile Asn Lys Thr Val Asp Gly Ser Thr Phe Ser
785                 790                 795                 800

Val Val Ile Pro Phe Leu Val Pro Gly Ile Arg Tyr Ser Val Glu Val
                805                 810                 815

Ala Ala Ser Thr Gly Ala Gly Ser Gly Val Lys Ser Glu Pro Gln Phe
                820                 825                 830

Ile Gln Leu Asp Ala His Gly Asn Pro Val Ser Pro Glu Asp Gln Val
            835                 840                 845

Ser Leu Ala Gln Gln Ile Ser Asp Val Val Lys Gln Pro Ala Phe Ile
850                 855                 860
```

```
Ala Gly Ile Gly Ala Ala Cys Trp Ile Ile Leu Met Val Phe Ser Ile
865                 870                 875                 880

Trp Leu Tyr Arg His Arg Lys Arg Asn Gly Leu Thr Ser Thr Tyr
                885                 890                 895

Ala Gly Ile Arg Lys Val Pro Ser Phe Thr Phe Thr Pro Thr Val Thr
            900                 905                 910

Tyr Gln Arg Gly Gly Glu Ala Val Ser Ser Gly Gly Arg Pro Gly Leu
        915                 920                 925

Leu Asn Ile Ser Glu Pro Ala Ala Gln Pro Trp Leu Ala Asp Thr Trp
    930                 935                 940

Pro Asn Thr Gly Asn Asn His Asn Asp Cys Ser Ile Ser Cys Cys Thr
945                 950                 955                 960

<210> SEQ ID NO 34
<211> LENGTH: 957
<212> TYPE: PRT
<213> ORGANISM: Homo sapiens

<400> SEQUENCE: 34

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
            260                 265                 270

Asp His Thr Leu Lys Ile Arg Lys Val Thr Ala Gly Asp Met Gly Ser
        275                 280                 285
```

```
Tyr Thr Cys Val Ala Glu Asn Met Val Gly Lys Ala Glu Ala Ser Ala
    290             295                 300
Thr Leu Thr Val Gln Glu Pro Pro His Phe Val Lys Pro Arg Asp
305             310                 315                 320
Gln Val Val Ala Leu Gly Arg Thr Val Thr Phe Gln Cys Glu Ala Thr
                325                 330                 335
Gly Asn Pro Gln Pro Ala Ile Phe Trp Arg Arg Glu Gly Ser Gln Asn
            340                 345                 350
Leu Leu Phe Ser Tyr Gln Pro Pro Gln Ser Ser Ser Arg Phe Ser Val
            355                 360                 365
Ser Gln Thr Gly Asp Leu Thr Ile Thr Asn Val Gln Arg Ser Asp Val
    370                 375                 380
Gly Tyr Tyr Ile Cys Gln Thr Leu Asn Val Ala Gly Ser Ile Ile Thr
385                 390                 395                 400
Lys Ala Tyr Leu Glu Val Thr Asp Val Ile Ala Asp Arg Pro Pro Pro
                405                 410                 415
Val Ile Arg Gln Gly Pro Val Asn Gln Thr Val Ala Val Asp Gly Thr
                420                 425                 430
Phe Val Leu Ser Cys Val Ala Thr Gly Ser Pro Val Pro Thr Ile Leu
            435                 440                 445
Trp Arg Lys Asp Gly Val Leu Val Ser Thr Gln Asp Ser Arg Ile Lys
    450                 455                 460
Gln Leu Glu Asn Gly Val Leu Gln Ile Arg Tyr Ala Lys Leu Gly Asp
465                 470                 475                 480
Thr Gly Arg Tyr Thr Cys Ile Ala Ser Thr Pro Ser Gly Glu Ala Thr
                485                 490                 495
Trp Ser Ala Tyr Ile Glu Val Gln Glu Phe Gly Val Pro Val Gln Pro
            500                 505                 510
Pro Arg Pro Thr Asp Pro Asn Leu Ile Pro Ser Ala Pro Ser Lys Pro
    515                 520                 525
Glu Val Thr Asp Val Ser Arg Asn Thr Val Thr Leu Ser Trp Gln Pro
        530                 535                 540
Asn Leu Asn Ser Gly Ala Thr Pro Thr Ser Tyr Ile Ile Glu Ala Phe
545                 550                 555                 560
Ser His Ala Ser Gly Ser Ser Trp Gln Thr Val Ala Glu Asn Val Lys
                565                 570                 575
Thr Glu Thr Ser Ala Ile Lys Gly Leu Lys Pro Asn Ala Ile Tyr Leu
            580                 585                 590
Phe Leu Val Arg Ala Ala Asn Ala Tyr Gly Ile Ser Asp Pro Ser Gln
            595                 600                 605
Ile Ser Asp Pro Val Lys Thr Gln Asp Val Leu Pro Thr Ser Gln Gly
    610                 615                 620
Val Asp His Lys Gln Val Gln Arg Glu Leu Gly Asn Ala Val Leu His
625                 630                 635                 640
Leu His Asn Pro Thr Val Leu Ser Ser Ser Ile Glu Val His Trp
                645                 650                 655
Thr Val Asp Gln Gln Ser Gln Tyr Ile Gln Gly Tyr Lys Ile Leu Tyr
            660                 665                 670
Arg Pro Ser Gly Ala Asn His Gly Glu Ser Asp Trp Leu Val Phe Glu
            675                 680                 685
Val Arg Thr Pro Ala Lys Asn Ser Val Val Ile Pro Asp Leu Arg Lys
    690                 695                 700
```

-continued

```
Gly Val Asn Tyr Glu Ile Lys Ala Arg Pro Phe Phe Asn Glu Phe Gln
705                 710                 715                 720

Gly Ala Asp Ser Glu Ile Lys Phe Ala Lys Thr Leu Glu Glu Ala Pro
            725                 730                 735

Ser Ala Pro Pro Gln Gly Val Thr Val Ser Lys Asn Asp Gly Asn Gly
        740                 745                 750

Thr Ala Ile Leu Val Ser Trp Gln Pro Pro Glu Asp Thr Gln Asn
    755                 760                 765

Gly Met Val Gln Glu Tyr Lys Val Trp Cys Leu Gly Asn Glu Thr Arg
770                 775                 780

Tyr His Ile Asn Lys Thr Val Asp Gly Ser Thr Phe Ser Val Val Ile
785                 790                 795                 800

Pro Phe Leu Val Pro Gly Ile Arg Tyr Ser Val Glu Val Ala Ala Ser
                805                 810                 815

Thr Gly Ala Gly Ser Gly Val Lys Ser Glu Pro Gln Phe Ile Gln Leu
            820                 825                 830

Asp Ala His Gly Asn Pro Val Ser Pro Glu Asp Gln Val Ser Leu Ala
        835                 840                 845

Gln Gln Ile Ser Asp Val Val Lys Gln Pro Ala Phe Ile Ala Gly Ile
    850                 855                 860

Gly Ala Ala Cys Trp Ile Ile Leu Met Val Phe Ser Ile Trp Leu Tyr
865                 870                 875                 880

Arg His Arg Lys Lys Arg Asn Gly Leu Thr Ser Thr Tyr Ala Gly Ile
                885                 890                 895

Arg Lys Val Pro Ser Phe Thr Phe Thr Pro Thr Val Thr Tyr Gln Arg
            900                 905                 910

Gly Gly Glu Ala Val Ser Ser Gly Gly Arg Pro Gly Leu Leu Asn Ile
        915                 920                 925

Ser Glu Pro Ala Ala Gln Pro Trp Leu Ala Asp Thr Trp Pro Asn Thr
    930                 935                 940

Gly Asn Asn His Asn Asp Cys Ser Ile Ser Cys Cys Thr
945                 950                 955
```

<210> SEQ ID NO 35
<211> LENGTH: 535
<212> TYPE: PRT
<213> ORGANISM: Homo sapiens

<400> SEQUENCE: 35

```
Val Glu Gln Asn Lys Leu Asn Lys Asp Tyr Arg Ala Asn Asp Thr Val
1               5                   10                  15

Pro Pro Thr Ile Pro Tyr Asn Gln Ser Tyr Asp Gln Asn Thr Gly Gly
            20                  25                  30

Ser Tyr Asn Ser Ser Asp Arg Gly Ser Ser Thr Ser Gly Ser Gln Gly
        35                  40                  45

His Lys Lys Gly Ala Arg Thr Pro Lys Val Pro Lys Gln Gly Gly Met
    50                  55                  60

Asn Trp Ala Asp Leu Leu Pro Pro Pro Ala His Pro Pro His
65                  70                  75                  80

Ser Asn Ser Glu Glu Tyr Asn Ile Ser Val Asp Glu Ser Tyr Asp Gln
                85                  90                  95

Glu Met Pro Cys Pro Val Pro Pro Ala Arg Met Tyr Leu Gln Gln Asp
            100                 105                 110

Glu Leu Glu Glu Glu Glu Asp Glu Arg Gly Pro Thr Pro Pro Val Arg
        115                 120                 125
```

```
Gly Ala Ala Ser Ser Pro Ala Val Ser Tyr Ser His Gln Ser Thr
    130                 135                 140
Ala Thr Leu Thr Pro Ser Pro Gln Glu Glu Leu Gln Pro Met Leu Gln
145                 150                 155                 160
Asp Cys Pro Glu Glu Thr Gly His Met Gln His Gln Pro Asp Arg Arg
                165                 170                 175
Arg Gln Pro Val Ser Pro Pro Pro Arg Pro Ile Ser Pro
            180                 185                 190
His Thr Tyr Gly Tyr Ile Ser Gly Pro Leu Val Ser Asp Met Asp Thr
            195                 200                 205
Asp Ala Pro Glu Glu Glu Asp Glu Ala Asp Met Glu Val Ala Lys
    210                 215                 220
Met Gln Thr Arg Arg Leu Leu Leu Arg Gly Leu Glu Gln Thr Pro Ala
225                 230                 235                 240
Ser Ser Val Gly Asp Leu Glu Ser Ser Val Thr Gly Ser Met Ile Asn
                245                 250                 255
Gly Trp Gly Ser Ala Ser Glu Glu Asp Asn Ile Ser Ser Gly Arg Ser
            260                 265                 270
Ser Val Ser Ser Ser Asp Gly Ser Phe Phe Thr Asp Ala Asp Phe Ala
        275                 280                 285
Gln Ala Val Ala Ala Ala Glu Tyr Ala Gly Leu Lys Val Ala Arg
    290                 295                 300
Arg Gln Met Gln Asp Ala Ala Gly Arg Arg His Phe His Ala Ser Gln
305                 310                 315                 320
Cys Pro Arg Pro Thr Ser Pro Val Ser Thr Asp Ser Asn Met Ser Ala
                325                 330                 335
Ala Val Met Gln Lys Thr Arg Pro Ala Lys Lys Leu Lys His Gln Pro
            340                 345                 350
Gly His Leu Arg Arg Glu Thr Tyr Thr Asp Asp Leu Pro Pro Pro Pro
        355                 360                 365
Val Pro Pro Pro Ala Ile Lys Ser Pro Thr Ala Gln Ser Lys Thr Gln
    370                 375                 380
Leu Glu Val Arg Pro Val Val Pro Lys Leu Pro Ser Met Asp Ala
385                 390                 395                 400
Arg Thr Asp Arg Ser Ser Asp Arg Lys Gly Ser Ser Tyr Lys Gly Arg
                405                 410                 415
Glu Val Leu Asp Gly Arg Gln Val Val Asp Met Arg Thr Asn Pro Gly
            420                 425                 430
Asp Pro Arg Glu Ala Gln Glu Gln Gln Asn Asp Gly Lys Gly Arg Gly
        435                 440                 445
Asn Lys Ala Ala Lys Arg Asp Leu Pro Pro Ala Lys Thr His Leu Ile
    450                 455                 460
Gln Glu Asp Ile Leu Pro Tyr Cys Arg Pro Thr Phe Pro Thr Ser Asn
465                 470                 475                 480
Asn Pro Arg Asp Pro Ser Ser Ser Ser Met Ser Ser Arg Gly Ser
                485                 490                 495
Gly Ser Arg Gln Arg Glu Gln Ala Asn Val Gly Arg Arg Asn Ile Ala
            500                 505                 510
Glu Met Gln Val Leu Gly Gly Tyr Glu Arg Gly Glu Asp Asn Asn Glu
        515                 520                 525
Glu Leu Glu Glu Thr Glu Ser
    530                 535
```

<210> SEQ ID NO 36
<211> LENGTH: 535
<212> TYPE: PRT
<213> ORGANISM: Homo sapiens

<400> SEQUENCE: 36

```
Val Glu Gln Asn Lys Leu Asn Lys Asp Tyr Arg Ala Asn Asp Thr Val
1               5                   10                  15

Pro Pro Thr Ile Pro Tyr Asn Gln Ser Tyr Asp Gln Asn Thr Gly Gly
            20                  25                  30

Ser Tyr Asn Ser Ser Asp Arg Gly Ser Ser Thr Ser Gly Ser Gln Gly
        35                  40                  45

His Lys Lys Gly Ala Arg Thr Pro Lys Val Pro Lys Gln Gly Gly Met
    50                  55                  60

Asn Trp Ala Asp Leu Leu Pro Pro Pro Ala His Pro Pro Pro His
65                  70                  75                  80

Ser Asn Ser Glu Glu Tyr Asn Ile Ser Val Asp Glu Ser Tyr Asp Gln
                85                  90                  95

Glu Met Pro Cys Pro Val Pro Pro Ala Arg Met Tyr Leu Gln Gln Asp
            100                 105                 110

Glu Leu Glu Glu Glu Asp Glu Arg Gly Pro Thr Pro Pro Val Arg
    115                 120                 125

Gly Ala Ala Ser Ser Pro Ala Ala Val Ser Tyr Ser His Gln Ser Thr
    130                 135                 140

Ala Thr Leu Thr Pro Ser Pro Gln Glu Glu Leu Gln Pro Met Leu Gln
145                 150                 155                 160

Asp Cys Pro Glu Glu Thr Gly His Met Gln His Gln Pro Asp Arg Arg
                165                 170                 175

Arg Gln Pro Val Ser Pro Pro Pro Arg Pro Ile Ser Pro Pro
            180                 185                 190

His Thr Tyr Gly Tyr Ile Ser Gly Pro Leu Val Ser Asp Met Asp Thr
        195                 200                 205

Asp Ala Pro Glu Glu Glu Asp Glu Ala Asp Met Glu Val Ala Lys
    210                 215                 220

Met Gln Thr Arg Arg Leu Leu Leu Arg Gly Leu Glu Gln Thr Pro Ala
225                 230                 235                 240

Ser Ser Val Gly Asp Leu Glu Ser Ser Val Thr Gly Ser Met Ile Asn
                245                 250                 255

Gly Trp Gly Ser Ala Ser Glu Glu Asp Asn Ile Ser Ser Gly Arg Ser
            260                 265                 270

Ser Val Ser Ser Ser Asp Gly Ser Phe Phe Thr Asp Ala Asp Phe Ala
        275                 280                 285

Gln Ala Val Ala Ala Ala Glu Tyr Ala Gly Leu Lys Val Ala Arg
    290                 295                 300

Arg Gln Met Gln Asp Ala Ala Gly Arg Arg His Phe His Ala Ser Gln
305                 310                 315                 320

Cys Pro Arg Pro Thr Ser Pro Val Ser Thr Asp Ser Asn Met Ser Ala
                325                 330                 335

Ala Val Met Gln Lys Thr Arg Pro Ala Lys Lys Leu Lys His Gln Pro
            340                 345                 350

Gly His Leu Arg Arg Glu Thr Tyr Thr Asp Asp Leu Pro Pro Pro Pro
        355                 360                 365

Val Pro Pro Pro Ala Ile Lys Ser Pro Thr Ala Gln Ser Lys Thr Gln
    370                 375                 380
```

-continued

```
Leu Glu Val Arg Pro Val Val Pro Lys Leu Pro Ser Met Asp Ala
385                 390             395                 400

Arg Thr Asp Arg Ser Ser Asp Arg Lys Gly Ser Ser Tyr Lys Gly Arg
                405             410                 415

Glu Val Leu Asp Gly Arg Gln Val Val Asp Met Arg Thr Asn Pro Gly
            420             425                 430

Asp Pro Arg Glu Ala Gln Glu Gln Gln Asn Asp Gly Lys Gly Arg Gly
        435             440                 445

Asn Lys Ala Ala Lys Arg Asp Leu Pro Pro Ala Lys Thr His Leu Ile
    450             455             460

Gln Glu Asp Ile Leu Pro Tyr Cys Arg Pro Thr Phe Pro Thr Ser Asn
465             470             475                 480

Asn Pro Arg Asp Pro Ser Ser Ser Ser Met Ser Ser Arg Gly Ser
            485             490                 495

Gly Ser Arg Gln Arg Glu Gln Ala Asn Val Gly Arg Arg Asn Ile Ala
            500             505             510

Glu Met Gln Val Leu Gly Gly Tyr Glu Arg Gly Glu Asp Asn Asn Glu
        515             520             525

Glu Leu Glu Glu Thr Glu Ser
530             535
```

The invention claimed is:

1. A monoclonal antibody capable of specifically recognizing ROBO1 existing on the surface of a cell, which is produced from a hybridoma having accession No. FERM BP-10921.

2. A hybridoma having accession No. FERM BP-10921.

3. A method for producing the monoclonal antibody according to claim 1, which comprises:
    culturing a hybridoma which produces a monoclonal antibody capable of specifically recognizing ROBO1 existing on the surface of a cell and allowing the hybridoma to produce the monoclonal antibody.

4. A tumor diagnostic agent used in PET, which comprises the monoclonal antibody according to claim 1 labeled with a radioactive metal.

5. The tumor diagnostic agent used in PET according to claim 4, wherein the radioactive metal is $^{64}$Cu.

* * * * *